United States Patent [19]
Sato et al.

[11] Patent Number: 5,498,601
[45] Date of Patent: Mar. 12, 1996

[54] PLATELET AGGREGATION-INHIBITING PEPTIDES

[75] Inventors: Yoshimi Sato; Yoshio Hayashi; Jun Katada, all of Kawasaki, Japan

[73] Assignee: Nippon Steel Corporation, Tokyo, Japan

[21] Appl. No.: 232,261

[22] PCT Filed: Sep. 7, 1993

[86] PCT No.: PCT/JP93/01262

§ 371 Date: May 6, 1994

§ 102(e) Date: May 6, 1994

[87] PCT Pub. No.: WO94/05696

PCT Pub. Date: Mar. 17, 1994

[30] Foreign Application Priority Data

Jul. 9, 1992 [JP] Japan ................................. 4-238624
Aug. 18, 1993 [JP] Japan ................................. 5-203962

[51] Int. Cl.$^6$ .......................... A61K 38/04; C07K 7/00
[52] U.S. Cl. ................. 514/17; 514/8; 530/322; 530/329; 530/330
[58] Field of Search .................. 530/322, 329, 530/330; 514/8, 17

[56] References Cited

FOREIGN PATENT DOCUMENTS

0275748A1 7/1987 European Pat. Off. .
0410767A1 1/1991 European Pat. Off. .

OTHER PUBLICATIONS

Ruggeri, Z. et al. (1986) Inhibition of platelet function with synthetic peptides designed to be high-affinity antagonists of fibrinogen binding to platelets. *Proc. Natl. Acad. Sci. USA* 83, 5708–5712. See entire article, especially Tables 1 and 2 on p. 5710.

*Primary Examiner*—Jill Warden
*Assistant Examiner*—Benet Prickril
*Attorney, Agent, or Firm*—Kenyon & Kenyon

[57] ABSTRACT

Novel peptide derivatives having RGD as a basic structure were found which have a platelet aggregation-inhibiting action, blood coagulation-inhibiting action and cell adhesion-inhibiting action.

Utlizing these effects of the peptide derivatives, the following agents which comprise the peptides as active ingredients were provided: platelet aggregation-inhibiting agents that are effective in thrombolus during and after the treatment of thrombolysis and thromboembolism and that can further prevent reobstruction and cardiac infarction; blood coagulation-inhibiting agents that can inhibit blood coagulation which is the main cause of thrombus formation during extracorporeal circulation; cell adhesion-inhibiting agents; tumor metastasis-inhibiting agents; and agents for protecting platelet preparations for blood transfusion.

In addition, the present invention intends to provide platelet preparation packs for blood transfusion, characterized in that the peptide dervatives are contained in platelet preparations for blood transfusion in packs.

36 Claims, 10 Drawing Sheets

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i i i ) HYPOTHETICAL: YES ( i v ) ANTI-SENSE: NO ( v i ) ORIGINAL SOURCE:
        ( A ) ORGANISM: N/A (synthetic)

( x i ) SEQUENCE DESCRIPTION: SEQ ID NO:1:

Xaa  Xaa  Arg  Gly  Asp  Xaa
    1                     5

( 2 ) INFORMATION FOR SEQ ID NO:2:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i i i ) HYPOTHETICAL: YES ( i v ) ANTI-SENSE: NO ( v i ) ORIGINAL SOURCE:
        ( A ) ORGANISM: N/A (synthetic)

( x i ) SEQUENCE DESCRIPTION: SEQ ID NO:2:

Trp  Ser  Arg  Gly  Asp  Xaa
    1                     5

( 2 ) INFORMATION FOR SEQ ID NO:3:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i i i ) HYPOTHETICAL: YES ( i v ) ANTI-SENSE: NO ( v i ) ORIGINAL SOURCE:

(A) ORGANISM: N/A (synthetic)

(x i) SEQUENCE DESCRIPTION: SEQ ID NO:3:

Trp Val Arg Gly Asp Xaa
1               5

(2) INFORMATION FOR SEQ ID NO:4:

(i) SEQUENCE CHARACTERISTICS:
        (A) LENGTH: 6 amino acids
        (B) TYPE: amino acid
        (D) TOPOLOGY: linear (i i) MOLECULE TYPE: peptide (i i i) HYPOTHETICAL: YES (i v) ANTI-SENSE: NO (v i) ORIGINAL SOURCE:
        (A) ORGANISM: N/A (synthetic)

(x i) SEQUENCE DESCRIPTION: SEQ ID NO:4:

Xaa Ser Arg Gly Asp Xaa
1               5

(2) INFORMATION FOR SEQ ID NO:5:

(i) SEQUENCE CHARACTERISTICS:
        (A) LENGTH: 5 amino acids
        (B) TYPE: amino acid
        (D) TOPOLOGY: linear (i i) MOLECULE TYPE: peptide (i i i) HYPOTHETICAL: YES (i v) ANTI-SENSE: NO (v i) ORIGINAL SOURCE:
        (A) ORGANISM: N/A (synthetic)

(x i) SEQUENCE DESCRIPTION: SEQ ID NO:5:

Xaa Arg Gly Asp Xaa
1               5

(2) INFORMATION FOR SEQ ID NO:6:

(i) SEQUENCE CHARACTERISTICS:
        (A) LENGTH: 6 amino acids
        (B) TYPE: amino acid
        (D) TOPOLOGY: linear (i i) MOLECULE TYPE: peptide (i i i) HYPOTHETICAL: YES (i v) ANTI-SENSE: NO (v i) ORIGINAL SOURCE:
        (A) ORGANISM: N/A (synthetic)

(x i) SEQUENCE DESCRIPTION: SEQ ID NO:6:

Phe Ser Arg Gly Asp Xaa
1               5

(2) INFORMATION FOR SEQ ID NO:7:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (iii) HYPOTHETICAL: YES (iv) ANTI-SENSE: NO (vi) ORIGINAL SOURCE:
    (A) ORGANISM: N/A (synthetic)

(xi) SEQUENCE DESCRIPTION: SEQ ID NO:7:

Trp Ala Arg Gly Asp Xaa
1                  5

(2) INFORMATION FOR SEQ ID NO:8:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (iii) HYPOTHETICAL: YES (iv) ANTI-SENSE: NO (vi) ORIGINAL SOURCE:
        (A) ORGANISM: N/A (synthetic)

(xi) SEQUENCE DESCRIPTION: SEQ ID NO:8:

Trp Xaa Arg Gly Asp Xaa
1                  5

(2) INFORMATION FOR SEQ ID NO:9:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (iii) HYPOTHETICAL: YES (iv) ANTI-SENSE: NO (vi) ORIGINAL SOURCE:
        (A) ORGANISM: N/A (synthetic)

(xi) SEQUENCE DESCRIPTION: SEQ ID NO:9:

Trp Gly Arg Gly Asp Xaa
1                  5

(2) INFORMATION FOR SEQ ID NO:10:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (iii) HYPOTHETICAL: YES (iv) ANTI-SENSE: NO (vi) ORIGINAL SOURCE:
        (A) ORGANISM: N/A (synthetic)

(xi) SEQUENCE DESCRIPTION: SEQ ID NO:10:

Pro Ser Arg Gly Asp Xaa
1                  5

( 2 ) INFORMATION FOR SEQ ID NO:11:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i i i ) HYPOTHETICAL: YES ( i v ) ANTI-SENSE: NO ( v i ) ORIGINAL SOURCE:
        ( A ) ORGANISM: N/A (synthetic)

( x i ) SEQUENCE DESCRIPTION: SEQ ID NO:11:

Pro  Gly  Arg  Gly  Asp  Xaa
    1                         5

( 2 ) INFORMATION FOR SEQ ID NO:12:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( i i i ) HYPOTHETICAL: YES ( i v ) ANTI-SENSE: NO ( v i ) ORIGINAL SOURCE:
        ( A ) ORGANISM: N/A (synthetic)

( x i ) SEQUENCE DESCRIPTION: SEQ ID NO:12:

Arg  Gly  Asp  Xaa
    1

( 2 ) INFORMATION FOR SEQ ID NO:13:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( i i i ) HYPOTHETICAL: YES ( i v ) ANTI-SENSE: NO ( v i ) ORIGINAL SOURCE:
        ( A ) ORGANISM: N/A (synthetic)

( x i ) SEQUENCE DESCRIPTION: SEQ ID NO:13:

Tyr  Ile  Gly  Ser  Arg
    1                     5

( 2 ) INFORMATION FOR SEQ ID NO:14:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( i i i ) HYPOTHETICAL: YES ( i v ) ANTI-SENSE: NO (vi) ORIGINAL SOURCE:
 (A) ORGANISM: N/A (synthetic)

(xi) SEQUENCE DESCRIPTION: SEQ ID NO:14:

Ile Lys Val Ala Val
1             5

PLATELET AGGREGATION-INHIBITING PEPTIDES

TECHNICAL FIELD

The present invention relates to novel peptides and the like having an inhibitory action on platelet aggregation, and platelet aggregation-inhibiting agents, blood coagulation-inhibiting agents for extracorporeal circulation, cell adhesion-inhibiting agents, tumor metastasis-inhibiting agents and agents for protecting platelet preparations for blood transfusion which comprise the novel peptides or the like as active ingredients as well as platelet preparation packs for blood transfusion which comprise the novel peptides in the platelet preparations for blood transfusion in the packs.

BACKGROUND ART

Platelets play an important role in hemostasis by adhering to the surface of a damaged blood vessel.

However, it is known that platelet aggregation is primarily responsible for the formation of thrombus and that the formed thrombus obstructs a blood vessel. This obstruction prevents the adequate supply of oxygen and nutrients to tissues and organs and thereby causes ischemic diseases in circulatory organs as represented by myocardial infarction and cerebral infarction. At present, the mortality rates of these ischemic diseases follow that of cancer, which has become a significant social problem.

When medical treatments involving the extracorporeal circulation of blood, as exemplified by the use of an artificial heart and lung during surgical operations and renal dialysis for patients with renal failure, are conducted, blood coagulation may be caused by the activation and aggregation of platelets, which greatly disturb the performance of such treatments.

Thus, the prevention of thrombus formation and blood coagulation is an important matter in avoiding the occurrence of ischemic diseases or in safely conducting extracorporeal circulation.

Platelets are activated by the binding, to receptors on a platelet membrane, of thrombin present in plasma, connective tissue proteins such as collagen present in subendothelial tissues that may become exposed by damage to a blood vessel and other substances. Platelets are also activated by the binding of released adenosine diphosphate (ADP), adrenaline, serotonin, thromboxane (TX) A2 and the like to membrane receptors in a manner like autosecretion. Two kinds of glycoprotein units which compose a fibrinogen receptor are presented on the cell surface and associated to form a receptor complex (gpIIbIIIa), whereby aggregation via a fibrinogen bridge is induced.

Patients with thrombasthenia characterized by congenital absence of gpIIb and gpIIIa do not have a capability for platelet aggregation. Therefore, it is clear that the binding of the gpIIbIIIa complex to fibrinogen is essential to platelet aggregation (Rouslahti et al., Science, 238, 491 (1987)).

Attempts have been made to prevent thrombus formation by the inhibition of platelet aggregation utilizing the properties of the gpIIbIIIa complex. For example, Coller et al. reported that an F(ab')$_2$ fragment of a monoclonal antibody against the gpIIbIIIa complex has a strong inhibitory action on platelet aggregation and verified that a platelet aggregation-inhibiting agent could be developed utlizing this action (Blood, 68, 783, (1986)).

Although it is recognized that the monoclonal antibody has the potential as a therapeutic agent for inhibiting platelet aggregation, there is an apprehension for the possible production of antibodies against the monoclonal antibody by its repeated administration, since it is in itself a large protein.

Therefore, it has been desired to develop platelet aggregation-inhibiting agents containing as active ingredients non-immunogenic small compounds that have the properties of antagonists to the gpIIbIIIa complex.

Studies on the binding of fibrinogen to the gpIIbIIIa complex have been conducted aggressively. These studies started with the finding of arginine-glycine-aspartic acid (RGD) as an amino acid sequence common to cell adhesive molecule by a series of studies conducted by Ruoslahti et al. (Ruoslahti et al., Nature 309, 30–33 (1984)). The study of receptors recognizing the RGD sequence verified that the gpIIbIIIa complex is a receptor classified in an integrin family recognizing the RGD sequence (Phillips et al., Blood, 71, 831– 843 (1988)) and that this complex especially recognizes two RGDF (-phenylalanine) sequences present in the fibrinogen molecule, thereby binding with the fibrinogen (Andrieux et al., J. Biol. Chem., 264, 9258– 9265 (1989)).

Furthermore, it is known that the gpIIbIIIa complex binds to von Willebrand factor, fibronectin, vitronectin and thrombospondin which have the RGD sequence as well as fibrinogen (Pytela et al., Science., 231, 1559 (1986) and Cell, 42, 439 (1985)).

It is expected from these findings that synthetic peptides containing the RGD sequence inhibit the binding of the gpIIbIIIa complex to fibrinogen and thereby inhibit platelet aggregation. In fact, it was reported that 400 μM of a synthetic peptide GRGDSP completely inhibited the aggregation of platelets activated by ADP (Plow et al., Proc. Natl. Acad. Sci. USA., 82, 8057–8061 (1985)). In addition, it has been verified that RGDS at concentrations of 46–50 μM inhibits 80–90% of platelet aggregation in a concentration-dependent manner (Plow et al., Blood, 70, 110–115 (1987)). Moreover, it has been revealed that a peptide RGDF exhibits platelet aggregation-inhibiting activity 4–5 times as strong as RGDS (Harfinest et al., 71, 132–136 (1988)).

Japanese unexamined patent publication (hereinafter referred to as "KOKAI") Nos. Hei 1-190699 and Hei 2-62892, EPO 422937 A1 and U.S. Pat. No. 4,952,562 (hereinafter referred to as "USP") disclose tetrapeptide derivatives containing the RGD peptide. KOKAI No. Sho 63- 215696 discloses derivatives consisting of peptides. KOKAI Nos. Hei 3- 118331 and Hei 2-62892 and WO 91/01331 disclose derivatives having the cyclic structure of the RGD peptide.

It should be noted here that blood is usually transfused in separate components that are selected in accordance with use and whole blood transfusion is rarely conducted today. A platelet preparation for blood transfusion for use in such component transfusion is the blood preparation produced by a method of formulating the whole blood obtained by blood donation or that produced by component donation using the apheresis method. In usual practice, this platelet preparation is charged in a special preservative bag made of polyolefin or polyvinyl chloride immediately after the preparation treatment and stored at room temperature while stirring.

It has recently become clear that the adhesion of cells to extracellar matrix proteins is related to various diseases. In particular, it is being unrevealed that the adhesion is closely related to the mechanism of reoccurrence of tumor due to tumor metastasis.

The number of cases in which tumor can be removed by surgery is increasing due to improvements in the techniques of early detection and surgical operational techniques by the establishment of methods of tumor diagnosis. However, the mortality rate of tumor is increasing. The reoccurrence of tumor resulting from the metastasis of tumor cells is predominantly responsible for the high mortality rate. It may well be said that the reoccurrence of tumor can be prevented fairly effectively if a substance capable of suppressing the metastasis of tumor is found. Up to now, no effective agent in suppressing the metastasis of tumor has been developed.

Although the mechanism of the metastasis of tumor is not completely understood, it has been gradually revealed by recent studies. The metastasis of tumor has two very important steps, that is, the release of tumor cells from the primary lesion into blood and lymph and the transfer of tumor cells from lymph into tissues. Extracellular matrix proteins which compose the basement membrane of blood vessels are believed to provide a foothold for cell transfer.

In the basement membrane, various extracellular matrix proteins having the RGD sequence are present, such as fibronectin, collagen, vitronectin and laminin. The RGD sequence plays a very important role in the adhesion of tumor cells to the extracellular matrix proteins. Therefore, it has been pointed out that compounds inhibiting the adhesion of tumor cell to the basement membrane of blood vessels, particularly RGD analogues can inhibit tumor cells from releasing into blood and transfering from the inside of a blood vessel to the outside thereof and thereby suppress the metastasis of tumor.

In recent years, in order to develop highly active agents having high in vivo stability, there have been aggressively conducted studies in which compounds having a structure which does not naturally occur are derived from RGD peptide as a key compound (Hartman et al., J. Med. Chem., 35, 4640–4642 (1992) and Callahan et al., ibid, 35, 3970–3972 (1992)). These compounds are useful as platelet aggregation-inhibiting agents for oral administration which are susceptible to the action of protease; however, they are expected to manifest toxicity (this problem often occurs in the derivation to non-natural structures) and to have such a side effect that the drugs are not metabolized but accumulated in the human body. Hence, there exists a strong concern for safety.

An improvement in the in vivo stability of compounds leads to the persistence of platelet aggregation-inhibiting action and blood coagulation-inhibiting action, thereby potentially inhibiting for a long period of time the important physiological actions inherently possessed by platelets, as exemplified by the inducement of hemorrhagic tendency and the like.

In particular, at the time of extracorporeal circulation or surgical operation, the persistence of platelet aggregation-inhibiting action and blood coagulation-inhibiting action becomes a problem. For example, it has been reported that even heparin that is a drug from an organism and which is actually administered to suppress blood coagulation has such a significant side effect that it acts beyond an appropriate period and thereby hemorrhagic tendency is induced (Tadao Akizawa, et al., NIHON RINSHO, vol. 43, 377–391 (1985)).

Accordingly, in the case where a platelet aggregation-inhibiting agent is deliberately used to inhibit temporarily the aggregation ability of platelets at the time of extracorporeal circulation or surgical operation, it is not only desired that it has an excellent platelet aggregation-inhibiting ability but also required that it has good safety characteristics in that it acts for a reasonable period of time while it is rapidly metabolized after inactivation to compounds having no side effects. As described above, the RGD peptides per se do not have such high platelet aggregation-inhibiting and blood coagulation-inhibiting actions as to warrant use in clinical practice. However, the RGD peptides have an excellent characteristic in that they are broken down by protease inherently present in an organism to amino acids which are safe and useful to the organism.

The inventors utilized this characteristic and produced highly active peptide derivatives that have various purposive working times in organisms, that have excellent platelet aggregation-inhibiting ability and blood coagulation-inhibiting ability and which have a structure that is as homologous as possible to naturally occurring peptides. An object of the present invention is to provide platelet aggregation-inhibiting agents comprising the peptides as active ingredients. A further object of the present invention is to provide blood coagulation-inhibiting agents having reduced side effects which are useful at the time of extracorporeal circulation and surgical operations.

At present, the platelet function (platelet aggregation ability) of the above described platelet preparations for blood transfusion is significantly reduced during storage or preservation, which is one of the factors that prevent useful blood transfusion. Since there is no method available today for successfully storing the platelet preparations while avoiding the reduction of the platelet function during storage, the establishment of an effective method for storing the platelet preparations is being studied in the world. Therefore, a still further object of the present invention is to provide agents for protecting platelet preparations for blood transfusion that comprise the peptides as active ingredients.

It is believed that the reduction of platelet function during storage is caused mainly by ① the activation and aggregation of platelets, which are produced by various physical stimulations that occur at the time of collecting blood, treating and storing preparations and ② the lowering of the pH of preservative solutions. Although improvements in preservative solutions and preservative systems for the purpose of pH control have been aggressively made in recent years, it can not be said that they are sufficiently effective at present.

In addition, on the basis of the idea that the reduction of platelet function during storage may be suppressed by inhibiting the aggregation of platelets, several trials of adding platelet aggregation-inhibiting substances such as aspirin, prostaglandin and the like to store blood have been made at an experimental level. However, these compounds have a fatal disadvantage in that they are not easily broken down in vivo and therefore, if platelet preparations comprising these compounds are transfused, the condition in which systemic blood is hard to coagulate is maintained for at least several hours. Therefore, they are not used in clinical practice.

The inventors believed that the reduction of the aggregation ability of platelets and the decrease in the number of platelets can be prevented by adding the aforementioned highly biodegradable and safe derivative peptides having a strong platelet aggregation-inhibiting activity to platelet preparations for blood transfusion. Thus, an additional object of the present invention is to develop compounds having the ability to protect platelets in preparation packs during storage.

Moreover, other objects of the present invention are to provide cell adhesion-inhibiting agents and tumor metastasis-inhibiting agents which comprise the above mentioned peptides as active ingredients, utilizing the cell adhesion-inhibiting action of the peptides of the present invention.

DISCLOSURE OF INVENTION

The development of platelet aggregation-inhibiting agents suitable for extracorporeal circulation which have reduced side effects requires that compounds of interest have structures as homologous as possible to naturally occurring peptides. The inventors produced highly active peptides having an appropriate working time by adding to RGD-like sequences compounds such as amino acids, vitamins and the like that have reduced side effects and which are useful to organisms. If the peptides are broken down, the added portions are received in an organism as inherently useful substances. In other words, the inventors found a series of compounds having various working times that are broken down in a generally short time in organisms and which have a high platelet aggregation-inhibiting activity, said compounds retaining in their structures the peptide skeletons that are almost intact and which are to be rapidly broken down in vivo. In addition, it was found that these compounds can be used as active ingredients for cell adhesion-inhibiting agents, tumor metastasis-inhibiting agents, and agents for protecting platelet preparations for blood transfusion.

The subject matters of the present invention are as follows:

(1) a peptide, a peptide derivative or a salt thereof, that are represented by the following general formula:

A—B—Arg—Gly—Asp—C—D    (I) SEQ ID NO:1 wherein A is a compound selected from the group consisting of an amino acid, an amino acid derivative, a vitamin, a vitamin derivative, a vitamin-like active substance, a derivative of the vitamin-like active substance, a base of nucleic acids, a derivative of the base of nucleic acids and hydantoin acetic acid, B is an amino acid, C is an amino acid having a hydrophobic functional group, and D is a hydroxy or amino group;

(2) the peptide, peptide derivative or salt thereof according to (1), wherein said amino acid or amino acid derivative as A is proline, thioproline, hydroxyproline, dehydroproline, 2-oxo-4-thiazolidine carboxylic acid, N-alkyl glycine or an imino acid derivative represented by the following general formula:

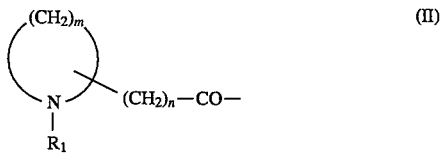

(II)

wherein $R_1$ is a hydrogen atom, —$(CH_2)_p$ $CH_3$ or —CO—$(CH_2)_p$ $CH_3$ group (p is an integer of 0–5), m is an integer of 2–5, n is an integer of 0–2, tryptophan or a tryptophan derivative represented by the following general formula:

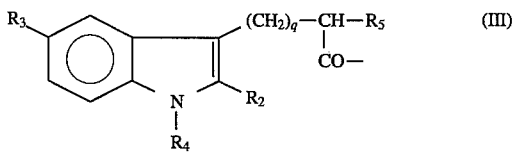

(III)

wherein $R_2$ is a hydrogen atom or an alkyl group, $R_3$ is a hydrogen atom or an O-alkyl group, $R_4$ is a hydrogen atom or an alkyl group, $R_5$ is a hydrogen atom, an amino or amino acyl group, and q is an integer of 0–3, pyroglutamic acid or 2-azetidinone-4-carboxylic acid;

(3) the peptide, peptide derivative or salt thereof according to (1), wherein said vitamin-like active substance or derivative of the vitamin-like active substance is orotic acid or hydroorotic acid;

(4) the peptide, peptide derivative or salt thereof according to (1)–(3), wherein said B is serine, glycine, valine, alanine, threonine or β-alanine;

(5) the peptide, peptide derivative or salt thereof according to any one of (1)–(4), wherein said C is tryptophan or phenylalanine;

(6) a platelet aggregation-inhibiting agent comprising the peptide, peptide derivative or salt thereof according to any one of (1)–(5) as an active ingredient;

(7) a blood coagulation-inhibiting agent for extracorporeal circulation comprising the peptide, peptide derivative or salt thereof according to any one of (1)–(5) as an active ingredient;

(8) a cell adhesion-inhibiting agent comprising the peptide, peptide derivative or salt thereof according to any one of (1)–(5) as an active ingredient;

(9) a tumor metastasis-inhibiting agent comprising the peptide, peptide derivative or salt thereof according to any one of (1)–(5) as an active ingredient;

(10) an agent for protecting platelet preparations for blood transfusion comprising the peptide, peptide derivative or salt thereof according to any one of (1)–(5) as an active ingredient;

(11) a platelet preparation pack for blood transfusion, characterized in that the agent for protecting platelets for blood transfusion according to any one of (1)–(5) is contained in a platelet preparation for blood transfusion.

The present invention will be explained hereinafter in detail.

① In the general formula (I), A is a compound selected from the group consisting of an amino acid, an amino acid derivative, a vitamin, a vitamin derivative, a vitamin-like active substance, a derivative of the vitamin-like active substance, a base of nucleic acids, a derivative of the base of nucleic acids and hydantoin acetic acid.

a) In the present invention, the term "amino acid" means a molecule having an amino and a carboxyl group in the molecule.

The preferred examples of the amino acid or amino acid derivative as A include imino acids such as proline, amino acids having a peptide bond (lactam) in the molecule, tryptophan and derivatives thereof.

In the case where the peptides or the like of the present invention are used as active ingredients of platelet aggregation-inhibiting agents or blood coagulation-inhibiting agents for extracorporeal circulation, the presence of proline in position A is preferred since it leads to a remarkable increase in the platelet aggregation-inhibiting activity and blood coagulation-inhibiting activity of the peptides and the like represented by general formula (I) (hereinafter referred to as the peptide(s) of the present invention).

In addition, the inventors found that if A is proline, the modification of the imino group in the proline lowered the platelet aggregation-inhibiting activity and blood coagulation-inhibiting activity of the peptide of the present invention, compared to the case where the imino group is not modified. Namely, the comparison between the compounds prepared in Examples 16 and 20 makes it clear that the amplification effect on the platelet aggregation-inhibiting activity due to the presence of proline is attributed to the imino group present in proline. Therefore, even in the case where A is not proline, the peptides of the present invention are capable of exhibiting a high platelet aggregation-inhibiting activity, if A is an amino acid having an imino group.

The proline derivatives may have other hetero atoms in their cyclic structure. Alternatively, a functional group may be added to their rings. Specific examples of them include thioproline, hydroxyproline, dehydroproline, oxothiazolidine carboxylic acid, N-methyl proline, N-acetyl proline and the like.

Preferred examples of the imino acids include N-alkyl glycine and cyclic imino acids represented by general formula (II) in various ring size ($R_1$ is a hydrogen atom). The alkyl portion of N-alkyl glycine is preferably a lower alkyl chain. Specific examples of them include N-methyl glycine (sarcosine), N-ethyl glycine, N-propyl glycine, N-isopropyl glycine and the like. In the case where $R_1$ in general formula (II) is other than a hydrogen atom (i.e., the imino group is modified), the platelet aggregation-inhibiting ability of the peptides of the present invention tends to decrease. However, this modification is effective in delaying the breakdown of the peptides from their N-terminus by enzymes in organisms and therefore is utilized to obtain derivatives having different rates of breakdown. In this case, $R_1$ is an alkyl or CO- alkyl group, preferably a lower alkyl or lower CO-alkyl group. Furthermore, p is preferably an integer of 0–5 in view of the appropriate degree of basicity and low steric hindrance.

The size of the cyclic structures of the cyclic imino acids can be selected in such a way that m ranges from 2 to 8. In order to lower the steric hindrance of the ring, m is preferably from 2 to 5.

Although the position of the carboxylic acid in general formula (II) does not directly influence the platelet aggregation-inhibiting activity of the peptides of the present invention, it is preferably 2-position which is adjacent to the imino group in view of the direction of the imino group which is a basic portion. An alkyl chain may be introduced between the ring and the carbonyl group. The value of n which is the number of the alkyl chains can be selected from the range from 0 to 6, preferably from 0 to 2 in view of the need to keep an appropriate distance from the cabonyl to the imino group.

Thus, preferred specific examples of the cyclic imino acids include L-2-azetidine carboxylic acid, o-, m-, p-piperidine carboxylic acids, pyrrolidine-3-carboxylic acid, pyrrolidine-2-acetic acid and the like.

Designing A in such a way that it becomes susceptible or unsusceptible to enzymatic breakdown in blood can ensure that the platelet aggregation-inhibiting agents and blood coagulation-inhibiting agents of the present invention which comprise the peptides of the present invention as active ingredients have a purposive working time.

In the case where use as blood coagulation-inhibiting agents for extracorporeal circulation is mainly intended, designing A in such a way that it becomes susceptible to enzymatic breakdown in blood can shorten the working time in an organism. Exemplary compounds include azetidine carboxylic acid which is a 4-membered ring compound and proline which is a 5-membered ring compound.

In the case where use as general platelet aggregation-inhibiting agents other than the above agents is intended, designing A in such a way that it becomes unsusceptible to enzymatic breakdown in blood can prolong the working time in organisms. Exemplary compounds include L-pipecolic acid which is a 6-membered ring compound and the like.

In general formula (II), the imino group may be replaced by an imide group (a lactam structure). This structure provides peptide compounds having not only appropriate stability against degradation enzymes but also high activity. Preferred examples thereof include pyroglutamic acid, 2-azetidinone-4-carboxylic acid and the like.

When A is tryptophan or its derivative, the platelet aggregation-inhibiting activity of the peptides of the present invention are also improved. This is believed to be due to the hydrophobic action of the indole ring in tryptophan.

In the tryptophan derivatives represented by general formula (III), $R_2$ is a hydrogen atom or an alkyl group, preferably a hydrogen atom or a lower alkyl group; $R_3$ is a hydrogen atom or O-alkyl group, preferably a hydrogen atom or a lower O-alkyl group; $R_4$ is a hydrogen atom or an alkyl group, preferably a hydrogen atom or a lower alkyl group; $R_5$ is a hydrogen atom, an amino or an amino acyl group. Typical examples of the amino acyl group include an amino acetyl and amino caproyl group.

In addition, the activity can also be improved when A is hydantoin acetic acid.

b) In the present invention, the kind of vitamins used as A is not particularly limited. For example, nicotinic acid, pantothenic acid, biotin, pteroylglutamic acid and the like may be used. In the present invention, the term "vitamin-like active substance" means one of a series of compounds having a similar physiological action to that of vitamins, which is not absolutely required to be exogenously ingested as nutrients in human and mammals (i.e., capable of autosynthesis in the body of human and mammals). Typical examples thereof include orotic acid, ribonucleic acid and the like.

Vitamins and vitamin-like active substances are characterized by being covalently bound to the peptide skeleton. Binding to the peptide skeleton requires the presence of a certain functional group. Exemplary functional groups include a carboxyl group and the like. Vitamins having no certain functional group can also be used if it is possible to derive a certain functional group with a simple treatment. One example is the case where a carboxylic acid is derived by hydrolysis of the amide in the nicotinic acid amide molecule. The bond between these substances and the peptide skeleton may be easily severed by enzymes present in organisms and thereby they may be changed to vitamins, vitamin-like active substances, intermediate products thereof or substantially non-toxic compounds. Examples of such bonds include an amide bond, an ester bond and the like.

Derivatives of vitamins and vitamin-like active substances include intermediate products of these compounds, associated compounds described in Biochemical Data Book (edited by Japanese Biochemical Society, Tokyo Kagaku Dojin) or compounds whose structures are partially modified in one or two positions. Typical examples thereof include 5-pyridoxic acid, biotin p-, L-sulfoxide, biotin sulfone, biocytin, pteroic acid, 10-formyl pteroic acid, 7,8-dihydro folic acid, (—)L—H, folic acid, homopteroic acid, 6-carboxyl pterin, dihydrolipoic acid, hydroorotic acid in which the double bond of a vitamin-like active substance orotic acid is reduced and the like.

c) The term "base of nucleic acid or its derivative" in the present invention generally means a nucleotide-constituting base component and its derivative which have the same structural feature as that described above concerning the vitamins and vitamin-like active substances. Preferred examples thereof include pyrimidine derivatives such as 5-carboxymethyl uracil, 5-carboxy thiouracil and the like.

② B is an amino acid and is not particularly limited in type. However, B is preferably an amino acid of relatively small steric hindrance such as serine, glycine, valine, alanine, threonine or β-alanine since amino acids having large steric hindrance or acidic amino acids tend to lower the platelet aggregation-inhibiting activity, blood coagulation-inhibiting activity and cell adhesion-inhibiting activity. Among these amino acids, serine is more preferred because of its high activity.

③ C is an amino acid which has a hydrophobic functional group as a hydrophobic domain binding to the receptor. Preferred examples thereof include tryptophan and phenylalanine.

④ D is a hydroxyl or amino group. When D is a hydroxyl group, the platelet aggregation-inhibiting activity, blood coagulation-inhibiting activity and cell adhesion-inhibiting activity tend to increase compared to the case where D is an amino group. The working time is longer in the case where D is an amino group. A suitable functional group can be selected in accordance with the purpose.

⑤ When the peptides of the present invention are used as active ingredients of blood coagulation-inhibiting agents for extracorporeal circulation, it is advantageous that they have different half-times.

The range of the half-times of the peptides of the present invention in plasma is from about 10 minutes to over 4 hours. Many of the peptides of the present invention have such a characteristic that they are rapidly broken down in the body. In most cases, the in vivo half-time ranges from an extremely short and unspecified time (within about 2 minutes) up to 10 minutes. Therefore, when the peptides are applied for extracorporeal circulation, they have an advantage in that they are stable in blood circulating in apparatus but that once they enter the body, they are rapidly broken down by various kinds of degradation enzymes to produce compounds useful to organisms and thereby lose the blood coagulation activity.

Therefore, the serious side effect that has been caused in the prior art by increased hemorrhagic tendency is due to the use of the antithrombotic agent heparin at the time of extracorporeal circulation can be eliminated by substituting the peptides of the present invention for heparin. Thus, the peptides of the present invention are extremely useful as active ingredients of blood coagulation-inhibiting agents for extracorporeal circulation.

Furthermore, in extracorporeal circulation in which the preferred working time of blood coagulation-inhibiting agents varies depending on the circulation apparatus and the purpose of their use, the peptides of the present invention can properly be used in accordance with the extracorporeal circulation time and the purpose of their use by utilizing the differences in working time (half-time).

When amino acids, peptides, protective groups, active groups and the like are designated herein by abbreviations, they should be comply with the definition by IUPAC and IBU or the conventional symbols used in the art. If an α-amino acid directly related to genetic control can have optical isomerism, it is to be understood that an L-isomer is meant unless otherwise indicated.

Examples of the abbreviations are shown below.

Ala or A: Alanine
Arg or R: Arginine
Asp or D: Asparatic acid
Gly or G: Glycine
Ser or S: Serine
Val or V: Valine
Thr or T: Threonine
Trp or W: Tryptophan
Phe or F: Phenylalanine
Pro or P: Proline
Boc: t-Butoxycarbonyl
$Bu^t$: t-Butyl
$OBu^t$: t-Butylester
Mtr: 4-Methoxy-2,3,6-trimethyl benzene sulfonyl
$P_{mc}$: 2,2,5,7,8-pentamethylchroman-6-sulfonyl
Fmoc: 9-Fluorenyl methoxycarbonyl The peptides and their analogues of the present invention can be easily synthesized with commercially available amino acids by simple procedures. For example, they can be prepared either in a liquid or solid phase by a conventional method used in peptide chemistry such as ones described in Schroder and Luhke, "The Peptides" vol. 1, Academic Press, New York, U.S.A. (1966), Nobuo Izumiya et al., "The Fundamentals and Experiments of Peptide Synthesis", Maruzen (1985) and the like. These preparation methods may be a column or batch method.

The condensation methods for forming peptide bonds include the azide method, acid chloride method, acid anhydride method, carbodiimide method, carbodiimide-additive method, active ester method, carbonyl imidazole method, redox method, enzymic method, the method using Woodward's reagent K and the like. In the case of performing a condensation reaction by a solid phase method, the acid anhydride method, carbodiimide method and active ester method may predominantly be used.

When a peptide chain is elongated by the solid phase method, the C-terminal amino acid is coupled to a support such as a resin that is insoluble in organic solvents to be used. In this case, the resin may be modified depending on the purpose by introducing a functional group for the purpose of bonding amino acids to the resin, by inserting a spacer between the resin and a functional group or by introducing a chain called "handle" which can be cleaved in various positions depending on the conditions. Exemplary resins include halomethyl resins (such as chloromethyl resin), oxymethyl resin, 4-(oxymethyl)phenylacetamide methyl resin, 4-(oxymethyl)-phenoxymethyl resin, resin for C-terminal amidation and the like.

Prior to the condensation reaction, carboxyl and amino groups, and guanidino group in arginine residue that do not take part in the condensation reaction may be protected by conventional and known techniques. In contrast with this, carboxyl and amino groups that directly take part in the condensation reaction may be activated.

As protective groups for the protection, those which are commonly used in the field of organic chemistry, as described in Greene, "Protective Groups in Organic Synthesis", John Willey & Sons, Inc. (1981), can be used.

Exemplary protective groups for hydroxyl group in an amino acid residue such as serine include t-butyl, benzyl, trimethylsilyl and tetrahydropyranyl groups and the like.

Exemplary protective groups for carboxyl group include commonly used and known protective groups such as various kinds of methyl ester, ethyl ester, benzyl ester, p-nitrobenzyl ester, t-butyl ester, cyclohexyl ester and the like.

Exemplary protective groups for amino group include benzyl oxycarbonyl, t-butoxycarbonyl, isobornyloxycarbonyl and 9-fluorenyl methoxycarbonyl groups and the like.

Exemplary protective groups for guanidino group in arginine residue include nitro, tosyl, mesitylenesulfonyl, 4-methoxy-2,3,6-trimethylbenzenesulfonyl and 2,2,5,7,8-pentamethylchroman-6-sulfonyl groups and the like.

Exemplary amino acids with an activated carboxyl group include the acid anhydride corresponding to the carboxyl group; azide; active esters with pentafluorophenol, 2,4-dinitrophenol, cyanomethyl alcohol, p-nitrophenol, N-hydroxysuccinimide, N-hydroxy-5-norbornene-2,3-dicarboximide, N-hydroxyphthalimide, and 1-hydroxybenzotriazole and the like.

Exemplary amino acids with an activated amino group include amide phosphate corresponding to the amino group.

The condensation reaction for peptide synthesis is usually carried out in a solvent. Exemplary solvents include chloroform, dichloromethane, ethyl acetate, N,N-dimethylformamide, dimethyl sulfoxide, pyridine, dioxane, tetrahydrofuran, N-methyl pyrrolidone, water, methanol and the like, and a mixture thereof. The condensation reaction can be carried out at a temperature of from −30° to 50° C. as usual.

The kind of the deprotection reaction of the protective groups in the peptide preparation process can be selected depending on the kind of the protective groups provided that the protective groups can be eliminated without affecting the peptide bonds. Exemplary deprotection reactions include a treatment with an acid such as hydrogen chloride, hydrogen bromide, anhydrous hydrogen fluoride, methanesulfonic acid, trifluoromethanesulfonic acid, trifluoro acetic acid, or a mixture thereof; a treatment with an alkali such as sodium hydroxide, potassium hydroxide, hydrazine, diethylamine, piperidine, or the like; a treatment with sodium in liquid ammonia; reduction with palladium on carbon; a silylation treatment with trimethylsilyl triflate, trimethylsilyl bromide or the like. In the above deblocking reaction with an acid or silylation agent, cation-trapping agents such as anisole, phenol, cresol, thioanisole and ethanedithiol are preferably added to carry out the deblocking reaction effectively.

The peptides synthesized by the solid phase method can be cleaved from the solid phase by conventional methods. Exemplary methods for cleaving the peptide include treatments with the acid or silylation agent described above.

The peptides thus prepared can be separated and purified in a conventional and known manner after the end of the series of reactions described above. For example, extraction, partition, reprecipitation, recrystallization, column chromatography and the like can be used to obtain the peptides in a more purified form.

The peptides of the present invention may be obtained in salt forms depending upon the reaction conditions in the preparation processes. Exemplary salts include inorganic acid salts such as hydrochloride, sulfate, nitrate, phosphate and the like; organic acid salts such as formate, acetate, propionate, glycolate, succinate, malate, tartrate, citrate, trifluoroacetate and the like; alkaline metal salts such as sodium and potassium salt and the like; alkaline earth metal salts such as calcium salt and the like; organic amine salts such as an ammonium, ethanolamine, triethylamine and dicyclohexylamine salt, and the like.

When the peptides of the present invention thus prepared are used as active ingredients of platelet aggregation-inhibiting agents, cell adhesion-inhibiting agents, tumor metastasis-inhibiting agents, and protective agents for platelet preparations for blood transfusion (hereinafter referred to as "platelet aggregation-inhibiting agents and the like"), they are formulated together with a solid or liquid pharmaceutically acceptable carrier or diluent, that is, an excipient, stabilizer, etc. In the pharmaceutical preparation, the ratio of the active ingredient to the carrier can be varied in a range of 1 to 90% by weight. The preparation may be in the form of granules, fine granules, powders, tablets, capsules, pills, liquids and solutions, and the like. The peptides may be orally administered in the form of bulk powders or they can be administered intravenously, intramuscularly or subcutaneously as injections. The injections may be prepared just before use from powders of the peptides of the present invention.

An organic or inorganic, solid or liquid pharmaceutically acceptable carrier or diluent suitable for oral, enteral or parenteral administration can be used to prepare the platelet aggregation-inhibiting agents and the like of the present invention. Water, gelatin, lactose, starch, magnesium stearate, talc, animal fats and oils, vegetable fats and oils, benzyl alcohol, gums, polyalkylene glycol, petroleum resins, coconut oil, lanolin, and all other carriers for medicines can be used as carriers or diluents for the platelet aggregation-inhibiting agents and the like of the present invention. Stabilizers, wetting agents, emulsifying agents, and salts for changing osmolarity or maintaining suitable pH of the preparation can be appropriately used as adjuvants.

If necessary, the platelet aggregation-inhibiting agents and the like of the present invention may contain other pharmaceutically active ingredients such as other kinds of platelet aggregation-inhibiting components in the case where they are used for the treatment of various diseases.

In the case of granules, fine granules, powders, tablets or capsules, the content of the active ingredient is preferably in the range from 5 to 80% by weight. In the case of liquids and solutions, the content of the active ingredient is preferably in the range from 1 to 30% by weight. Furthermore, in the case of injections, the content of the active ingredient is preferably in the range from 1 to 10% by weight.

When the platelet aggregation-inhibiting agents and the like are to be administered orally, the clinical dose of the active ingredient is preferably in the range from 500 to 1000 mg per day for adult patient, which can be varied depending on the age of the patient, severity of the disease to be treated and the like. The platelet aggregation-inhibiting agents and the like can be administered in the aforementioned daily dose either once a day, or twice or three times a day at suitable intervals. In the case of injections, the dose of the active ingredient is preferably in the range from one to several hundreds mg per injection for adult patient.

Some of the peptides of the present invention are characterized by high in vivo degradability. If the blood concentrations of these compounds are required to be maintained at high levels, they may be continuously injected by means of drip infusion and the like. In this case, the amount of injection is suitably in the range from 50 to 500 mg/kg per hour, which can be reduced in the case of combination with other drugs.

When the peptides of the present invention are used for extracorporeal circulation, they can be used in the form of injections and drip infusions. The position and dose of administration may be varied depending on the kind of extracorporeal circulation system, their duration time and the like. For example, the peptides can be injected or infused continuously in a dose of from 1 to 100 mg/kg per hour from the inlet to an extracorporeal circulation system. Irrespective of whether they are used singly or in combination with other drugs, the peptides are effective in a smaller dose in extracorporeal circulation systems than in vivo where degradation enzymes are present in large amounts.

It is believed that if the peptides of the present invention are combined with heparin which is used as a blood coagulation-inhibiting agent in the prior art, two important routes of blood coagulation, i.e., platelet aggregation and coagulation systems, are inhibited and thereby inhibit blood coagulation completely. In addition, since synergism of both kinds of drugs is expected, the use of heparin having the already described unwanted side effects can be reduced.

Furthermore, the combinations of the peptides of the present invention with citric acid, protease-inhibiting agents such as futhan, fibrinolytic agents such as t-PA and the like are believed to be effective.

The form of the platelet preparation packs of the present invention for blood transfusion which are characterized in that the agents for protecting platelets for blood transfusion of the present invention are contained in platelet preparations for blood transfusion are not particularly limited. All of the forms of platelet preparation packs for blood transfusion that are commonly used in clinical practice can be employed. Specific examples include the forms of bags, bottles and the like. The materials therefor also are not particularly limited. For example, poly-vinyl materials capable of inhibiting the adsorption of the active ingredient as much as possible, such as polyvinyl chloride, polyolefins and the like can be used as materials for the bags; plastic and glass materials can be used as materials for the bottles. The agents of the present invention for protecting platelets for blood transfusion can be added at a final concentration of from 1 μM to 1 mM, preferably from 10 μM to 50 μM in terms of the amount of the peptides of the present invention based on the amount of platelet components. Of course, other components that are usually added to platelet preparation packs for blood transfusion can be added together with the agents of the present invention for protecting platelets for blood transfusion.

Example

Figure 1:
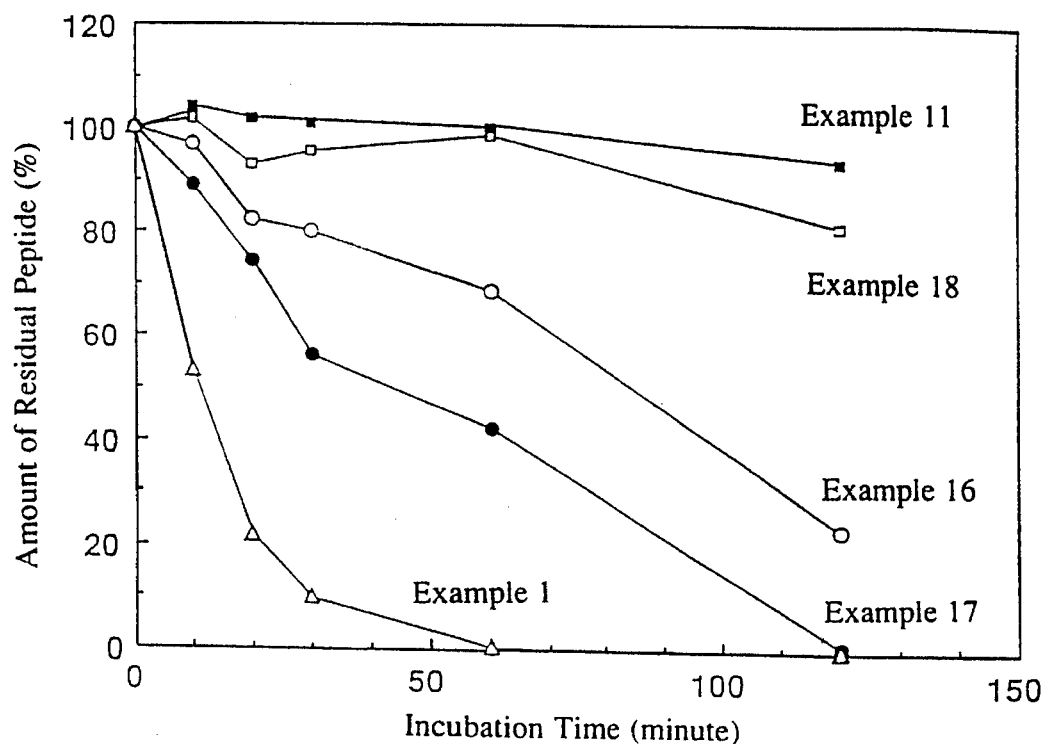
FIG. 1 is a graph showing the stability of synthetic peptides in human plasma.

The present invention will be explained hereinafter in greater detail with reference to the following working examples. It should, however, be noted that the scope of the present invention is not limited by these examples.

[Synthesis of compounds]

[Example 1]

Synthesis of the peptide represented by the following formula (1)

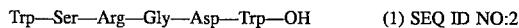
Trp—Ser—Arg—Gly—Asp—Trp—OH    (1) SEQ ID NO:2 p-Alkoxybenzyl alcohol type resin represented by the following formula (2) (the amount of Trp introduced: 0.87 meq/g; BACHEM Co.) (0.275 g; 0.25 mmol)

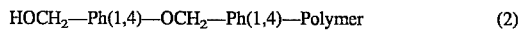
$HOCH_2$—Ph(1,4)—$OCH_2$—Ph(1,4)—Polymer    (2)

was placed in a reaction container. $F_{mo\ c}$—Trp was introduced in the form of active ester in the presence of DMAP and thereafter shaking and filtering steps were repeated as listed in Table 1 to obtain a protected peptide resin represented by the following general formula (3).

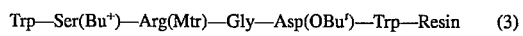
Trp—Ser($Bu^t$)—Arg(Mtr)—Gly—Asp($OBu^t$)—Trp—Resin    (3)

TABLE 1

| Steps | Reagents or Solvents | Amounts of use (ml/step) | Time (minute) | The number of Times |
|---|---|---|---|---|
| 1. | DMF | 30 | 1 | 6 |
| 2. | 20% Piperidine/DMF | 6 | 2 | 1 |
| 3. | 20% Piperidine/DMF | 6 | 20 | 1 |
| 4. | DMF | 50 | 1 | 10 |
| 5. | $F_{mo\ c}$-amino-acid & HOBT/DMF (3 eq each) | 6 | 2* | 1 |
| 6. | DIPCD**(3 eq) | 6 | 120 | 1 |

*proceed to the next step without removing the reagent or solvent after shaking.
**Diisopropylcarbodiimide The obtained protected peptide resin was treated with 1M of trimethylsilyl bromide and 1M of thioanisole in the presence of m-cresol and ethanedithiol in trifluoroacetic acid at 0° C. for one hour. Trimethylsilyl bromide was distilled off in a nitrogen gas stream and thereafter the resin was removed by filtration. Diethyl ether was added to the filtrate under ice-cooling to obtain a peptide cleaved from the resin as a powder. The powder was washed with diethyl ether. The washed peptide was desalted by gel permeation chromatography using Sephadex G-10 (Pharmacia Co.) as a support and lyophilized to obtain a crude peptide. The crude peptide was purified by high pressure liquid chromatography (HPLC) (column: ODS 5$C_{18}$ (μbondasphere, ⌀20×150 mm), mobile phase: (A) 0.1% TFA, (B) 100% $CH_3CN$/0.1% TFA, gradient: (A):(B)=80:20 to (A):(B)=70:30, 20 minutes, flow rate: 17 ml/min). The acetate of the peptide was obtained by gel filtration using Sephadex G-25 as a support and lyophilized to obtain 100 mg of the titled peptide represented by formula (1).

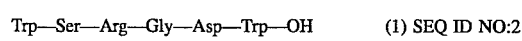
Trp—Ser—Arg—Gly—Asp—Trp—OH    (1) SEQ ID NO:2

Amino acid analysis (6N HCl+phenol, 24 hr, 110° C.)

In this assay, tryptophan can not be detected because it is degradated during acid hydrolysis. Amino acids whose standards are not present can not be detected because amino acids used as external standards for the determination are standard amino acids.

Asp 0.90 (1)
Ser 1.00 (1)
Gly 1.11 (1)
Trp—(2)
Arg 1.03 (1)

HPLC analysis

A spectrum of analytical HPLC using Cosmosil 5C18-AR (⌀4.6× 200 mm) column (Nacalai tesque Co.) at a flow rate of 1.0 ml/min by elution in a gradient of acetonitrile of 10–40% (60 min) in 0.1% TFA indicated a single peak at a retention time of 29.0 minutes. FAB-MS: M+H Calculated 806.3, Found 806

[Example 2]

Synthesis of the peptide represented by the following formula (4)

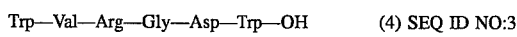

Trp—Val—Arg—Gly—Asp—Trp—OH        (4) SEQ ID NO:3

The titled peptide (100 mg) was synthesized by the same procedure as in Example 1.

Amino acid analysis (6N HCl+phenol, 24 hr, 110° C.)

Asp 0.95 (1)
Val 1.07 (1)
Gly 1.24 (1)
Trp—(2)
Arg 1.00 (1)

HPLC analysis

A spectrum of analytical HPLC using Cosmosil 5C18-AR (⌀4.6× 200 mm) column at a flow rate of 1.0 ml/min by elution in a gradient of acetonitrile of 10–40% (40 min) in 0.1% TFA indicated a single peak at a retention time of 24.0 minutes.

FAB-MS: M+H Calculated 818.4, Found 814

[Example 3]

Synthesis of the peptide represented by the following formula (5)

CH₃CO—Trp—Ser—Arg—Gly—Asp—
Trp—NH₂        (5) SEQ ID NO:4

The C-terminal amidated resin represented by the following general formula (6) (the amount of Trp introduced: 0.6 meq/g; BACHEM Co.) (0.45 g; 0.25 mmol)

CH₃O—Ph(1,4)—CH(NH—F$_{moc}$)—Ph(1,4)—O(CH₂)₃CONH—
CH(CH₃)—CONH— CH₂—Ph—polyme        (6)

was placed in a reaction container. Shaking and filtering steps were repeated as listed in the aforementioned Table 1 to obtain NH₂—Trp—Ser(Bu ')—Arg(Mtr)—Gly—Asp(OBu')—Trp—C—terminal amidated resin (7).

One equivalent of this resin was condensed with 3 equivalents of acetic anhydride in the presence of N-hydroxybenzotriazole (HOBT, 3 eq) in dimethylformamide (DMF) to obtain CH₃CO—Trp—Ser(Bu')—Arg(Mtr)— Gly—Asp(OBu')—Trp—C—terminal amidated resin (8).

The titled peptide (20 mg) was obtained from the obtained protected peptide resin by the same method as used in Example 1.

Amino acid analysis (6N HCl+phenol, 24 hr, 110° C.)

Asp 0.95 (1)
Ser 1.00 (1)

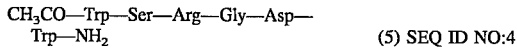

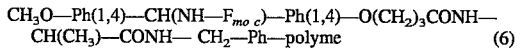

Gly 1.14 (1)
Trp—(2)
Arg 0.96 (1)

HPLC analysis

A spectrum of analytical HPLC using Cosmosil 5C18-AR (⌀4.6× 200 mm) column at a flow rate of 1.0 ml/min by elution in a gradient of acetonitrile of 10–40% (40 min) in 0.1% TFA indicated a single peak at a retention time of 25.0 minutes.

FAB-MS: M+H Calculated 847.4, Found 847

[Example 4]

Synthesis of the peptide represented by the following formula (9)

5-Methoxyindole-3-acetyl—Ser—Arg—Gly—Asp—
Trp—OH        (9) SEQ ID NO:4

The titled peptide (100 mg) was synthesized by the same procedure as in Example 1.

Amino acid analysis (6N HCl+phenol, 24 hr, 110° C.)

Asp 0.89 (1)
Ser 1.00 (1)
Gly 1.12 (1)
Trp—(1)
Arg 0.99 (1)

HPLC analysis

A spectrum of analytical HPLC using Cosmosil 5C18-AR (⌀4.6× 200 mm) column at a flow rate of 1.0 ml/min by elution in a gradient of acetonitrile of 10–40% (40 min) in 0.1% TFA indicated a single peak at a retention time of 28.0 minutes.

FAB-MS: M+H Calculated 807.3, Found 807

[Example 5]

Synthesis of the peptide represented by the following formula (10)

2-Methylindole-3-acetyl—Ser—Arg—Gly—Asp—
Trp—OH        (10) SEQ ID NO:4

The titled peptide (100 mg) was synthesized by the same procedure as in Example 1.

Amino acid analysis (6N HCl+phenol, 24 hr, 110° C.)

Asp 0.88 (1)
Ser 1.00 (1)
Gly 1.12 (1)
Trp—(1)
Arg 0.99 (1)

HPLC analysis

A spectrum of analytical HPLC using Cosmosil 5C18-AR (⌀4.6× 200 mm) column at a flow rate of 1.0 ml/min by elution in a gradient of acetonitrile of 10–40% (40 min) in 0.1% TFA indicated a single peak at a retention time of 28.5 minutes.

FAB-MS: M+H Calculated 791.4, Found 791

[Example 6]

Synthesis of the peptide represented by the following formula (11)

Indole-3-butanoyl—Ser—Arg—Gly—Asp—
Trp—OH        (11) SEQ ID NO:5

The titled peptide (100 mg) was synthesized by the same procedure as in Example 1.

Amino acid analysis (6N HCl+phenol, 24 hr, 110° C.)

Asp 0.87 (1)
Ser 1.00 (1)
Gly 1.13 (1)
Trp—(1)

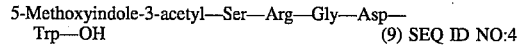

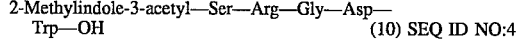

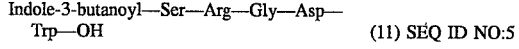

Arg 1.01 (1)
HPLC analysis

A spectrum of analytical HPLC using Cosmosil 5C18-AR (⌀4.6× 200 mm) column at a flow rate of 1.0 ml/min by elution in a gradient of acetonitrile of 10–40% (40 min) in 0.1% TFA indicated a single peak at a retention time of 33.0 minutes.
FAB-MS: M+H Calculated 805.4, Found 805

[Example 7]

Synthesis of the peptide represented by the following formula (12)

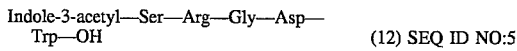
Indole-3-acetyl—Ser—Arg—Gly—Asp—Trp—OH (12) SEQ ID NO:5

The titled peptide (100 mg) was synthesized by the same procedure as in Example 1.
Amino acid analysis (6N HCl+phenol, 24 hr, 110° C.)

Asp 0.93 (1)
Ser 1.00 (1)
Gly 1.08 (1)
Trp—(1)
Arg 1.12 (1)
HPLC analysis

A spectrum of analytical HPLC using Cosmosil 5C18-AR (⌀4.6× 200 mm) column at a flow rate of 1.0 ml/min by elution in a gradient of acetonitrile of 10–40% (40 min) in 0.1% TFA indicated a single peak at a retention time of 27.0 minutes.
FAB-MS: M+H Calculated 777.3, Found 777

[Example 8]

Synthesis of the peptide represented by the following formula (13)

Phe—Ser—Arg—Gly—Asp—Phe—OH (13) SEQ ID NO:6

The titled peptide (100 mg) was synthesized by the same procedure as in Example 1.
Amino acid analysis (6N HCl+phenol, 24 hr, 110° C.)

Asp 1.00 (1)
Ser 1.01 (1)
Gly 1.00 (1)
Phe 1.83 (2)
Arg 1.04 (1)
HPLC analysis

A spectrum of analytical HPLC using Cosmosil 5C18-AR (⌀4.6× 200 mm) column at a flow rate of 1.0 ml/min by elution in a gradient of acetonitrile of 10–40% (60 min) in 0.1% TFA indicated a single peak at a retention time of 21.0 minutes.
FAB-MS: M+H Calculated 728.3, Found 728

[Example 9]

Synthesis of the peptide represented by the following formula (13)

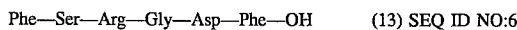
Orotyl—Ser—Arg—Gly—Asp—Trp—OH (13) SEQ ID NO:5

The titled peptide (100 mg) was synthesized by the same procedure as in Example 1.
Amino acid analysis (6N HCl+phenol, 24 hr, 110° C.)

Asp 0.86 (1)
Ser 1.00 (1)
Gly 1.26 (1)
Trp—(1)
Arg 1.00 (1)
HPLC analysis

A spectrum of analytical HPLC using Cosmosil 5C18-AR (⌀4.6× 200 mm) column at a flow rate of 1.0 ml/min by elution in a gradient of acetonitrile of 10–40% (60 min) in 0.1% TFA indicated a single peak at a retention time of 20.0 minutes.
FAB-MS: M+H Calculated 758.3, Found 758

[Example 10]

Synthesis of the peptide represented by the following formula (14)

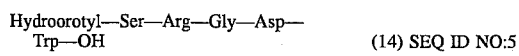
Hydroorotyl—Ser—Arg—Gly—Asp—Trp—OH (14) SEQ ID NO:5

The titled peptide (100 mg) was synthesized by the same procedure as in Example 1.
Amino acid analysis (6N HCl+phenol, 24 hr, 110° C.)

Asp 1.35 (1)
Ser 0.87 (1)
Gly 1.00 (1)
Trp—(1)
Arg 0.97 (1)
HPLC analysis

A spectrum of analytical HPLC using Cosmosil 5C18-AR (⌀4.6× 200 mm) column at a flow rate of 1.0 ml/min by elution in a gradient of acetonitrile of 10–40% (60 min) in 0.1% TFA indicated a single peak at a retention time of 20.0 minutes.
FAB-MS: M+H Calculated 760.3, Found 760

[Example 11]

Synthesis of the peptide represented by the following formula (15)

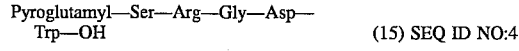
Pyroglutamyl—Ser—Arg—Gly—Asp—Trp—OH (15) SEQ ID NO:4

The titled peptide (100 mg) was synthesized by the same procedure as in Example 1.
Amino acid analysis (6N HCl+phenol, 24 hr, 110° C.)

Asp 0.86 (1)
Ser 1.00 (1)
Glu 1.12 (1)
Gly 1.22 (1)
Trp—(1)
Arg 1.13 (1)
HPLC analysis A spectrum of analytical HPLC using Cosmosil 5C18-AR (⌀4.6× 200 mm) column at a flow rate of 1.0 ml/min by elution in a gradient of acetonitrile of 10–40% (60 min) in 0.1% TFA indicated a single peak at a retention time of 14.0 minutes.
FAB-MS: M+H Calculated 731.3, Found 731

[Example 12]

Synthesis of the peptide represented by the following formula (16)

Trp—Ala—Arg—Gly—Asp—Trp—OH (16) SEQ ID NO:7

The titled peptide (100 mg) was synthesized by the same procedure as in Example 1.
Amino acid analysis (6N HCl+phenol, 24 hr, 110° C.)

Asp 0.92 (1)
Ala 1.00 (1)
Gly 1.00 (1)
Trp—(2)
Arg 1.13 (1)
HPLC analysis

A spectrum of analytical HPLC using Cosmosil 5C18-AR (⌀4.6× 200 mm) column at a flow rate of 1.0 ml/min by elution in a gradient of acetonitrile of 10–40% (60 min) in 0.1% TFA indicated a single peak at a retention time of 30.0 minutes.
FAB-MS: M+H Calculated 790.3, Found 790

[Example 13]

Synthesis of the peptide represented by the following formula (17)

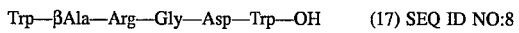

Trp—βAla—Arg—Gly—Asp—Trp—OH    (17) SEQ ID NO:8

The titled peptide (100 mg) was synthesized by the same procedure as in Example 1.
Amino acid analysis (6N HCl+phenol, 24 hr, 110° C.)

Asp 0.90 (1)

β Ala—(1)

Gly 1.00 (1)

Trp—(2)

Arg 1.07 (1)

HPLC analysis

A spectrum of analytical HPLC using Cosmosil 5C18-AR (⌀4.6× 200 mm) column at a flow rate of 1.0 ml/min by elution in a gradient of acetonitrile of 10–40% (60 min) in 0.1% TFA indicated a single peak at a retention time of 30.0 minutes.
FAB-MS: M+H Calculated 790.3, Found 790

[Example 14]

Synthesis of the peptide represented by the following formula (18)

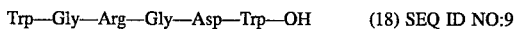

Trp—Gly—Arg—Gly—Asp—Trp—OH    (18) SEQ ID NO:9

The titled peptide (100 mg) was synthesized by the same procedure as in Example 1.
Amino acid analysis (6N HCl+phenol, 24 hr, 110° C.)

Asp 0.90 (1)

Gly 2.06 (2)

Trp—(2)

Arg 1.00 (1)

HPLC analysis

A spectrum of analytical HPLC using Cosmosil 5C18-AR (⌀4.6× 200 mm) column at a flow rate of 1.0 ml/min by elution in a gradient of acetonitrile of 10–40% (60 min) in 0.1% TFA indicated a single peak at a retention time of 30.0 minutes.
FAB-MS: M+H Calculated 776.3, Found 776

[Example 15]

Synthesis of the peptide represented by the following formula (19)

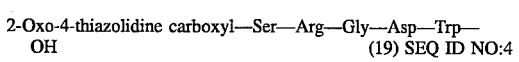

2-Oxo-4-thiazolidine carboxyl—Ser—Arg—Gly—Asp—Trp—OH    (19) SEQ ID NO:4

The titled peptide (100 mg) was synthesized by the same procedure as in Example 1.
Amino acid analysis (6N HCl+phenol, 24 hr, 110° C.)

Asp 0.90 (1)

Ser 1.00 (1)

Gly 1.06 (1)

Trp—(1)

Arg 1.00 (1)

HPLC analysis

A spectrum of analytical HPLC using Cosmosil 5C18-AR (⌀4.6× 200 mm) column at a flow rate of 1.0 ml/min by elution in a gradient of acetonitrile of 10–40% (60 min) in 0.1% TFA indicated a single peak at a retention time of 24.0 minutes.
FAB-MS: M+H Calculated 749.3, Found 749

[Example 16]

Synthesis of the peptide represented by the following formula (20)

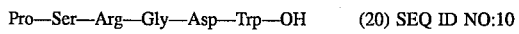

Pro—Ser—Arg—Gly—Asp—Trp—OH    (20) SEQ ID NO:10 p-Alkoxybenzyl alcohol type resin represented by formula (2) (the amount of Trp introduced: 0.87 meq/g; BACHEM Co.) (0.275 g; 0.25 mmol) was placed in a reaction container. $F_{mo\,c}$—Trp was introduced in the form of active ester in the presence of DMAP and thereafter shaking and filtering steps were repeated as listed in Table 1 to obtain a protected peptide resin represented by the following general formula (21).

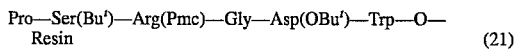

Pro—Ser(Bu$^t$)—Arg(Pmc)—Gly—Asp(OBu$^t$)—Trp—O—Resin    (21)

The obtained protected peptide resin was treated in the presence of m-cresol, ethanedithiol and thioanisole in trifluoroacetic acid at 0° C. for one hour. Trifluoroacetic acid was distilled off with an evaporator and thereafter the resin was removed by filtration. Diethyl ether was added to the filtrate under ice-cooling to obtain the peptide (as a powder) cleaved from the resin. The powder was washed with diethyl ether. The washed peptide was desalted by gel permeation chromatography using Sephadex G-10 (Pharmacia Co.) as a support and lyophilized to obtain a crude peptide. The crude peptide was purified by HPLC (column: ODS 5C$_{18}$ (μ bondashere, ⌀20×150 mm), mobile phase: (A) 0.1% TFA, (B) 100% CH$_3$CN/0.1% TFA, gradient: (A):(B)=90:10 to (A):(B)=70:30, flow rate: 17 ml/min). The acetate of the peptide was obtained by gel filtration using Sephadex G-25 (Pharmacia Co.) as a support and lyophilized to obtain 40 mg of the titled peptide of the present invention represented by the following formula.

Pro—Ser—Arg—Gly—Asp—Trp—OH

Amino acid analysis (6N HCl+phenol, 24 hr, 110° C.)

Asp 0.85 (1)

Ser 1.00 (1)

Gly 1.23 (1)

Trp—(1)

Arg 1.13 (1)

Pro 1.31 (1)

HPLC analysis

A spectrum of analytical HPLC using Cosmosil 5C18-AR (⌀4.6× 200 mm) column (Nakalai tesque Co.) at a flow rate of 1.0 ml/min by elution in a gradient of acetonitrile of 10–40% (60 min) in 0.1% TFA indicated a single peak at a retention time of 18.0 minutes.
FAB-MS: M+H Calculated 717.3, Found 717

[Example 17]

Synthesis of the peptide represented by the following formula (22)

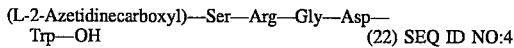

(L-2-Azetidinecarboxyl)—Ser—Arg—Gly—Asp—Trp—OH    (22) SEQ ID NO:4

The titled peptide (40 mg) was synthesized by the same procedure as in Example 16.
Amino acid analysis (6N HCl+phenol, 24 hr, 110° C.)

Asp 0.93 (1)

Ser 1.00 (1)

Gly 1.19 (1)

Trp—(1)

Arg 1.15 (1)

HPLC analysis

A spectrum of analytical HPLC using Cosmosil 5C18-AR (⌀4.6×200 mm) column at a flow rate of 1.0 ml/min by elution in a gradient of acetonitrile of 10–40% (60 min) in 0.1% TFA indicated a single peak at a retention time of 18.0 minutes.
FAB-MS: M+H Calculated 703.3, Found 703

[Example 18]

Synthesis of the peptide represented by the following formula (23)

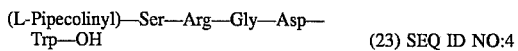
(L-Pipecolinyl)—Ser—Arg—Gly—Asp—Trp—OH (23) SEQ ID NO:4

The titled peptide (40 mg) was synthesized by the same procedure as in Example 16.
Amino acid analysis (6N HCl+phenol, 24 hr, 110° C.)
Asp 0.91 (1)
Ser 1.00 (1)
Gly 1.15 (1)
Trp—(1)
Arg 1.11 (1)
HPLC analysis A spectrum of analytical HPLC using Cosmosil 5C18-AR (ø4.6× 200 mm) column at a flow rate of 1.0 ml/min by elution in a gradient of acetonitrile of 10–40% (60 min) in 0.1% TFA indicated a single peak at a retention time of 20.0 minutes.
FAB-MS: M+H Calculated 731.3, Found 731

[Example 19]

Synthesis of the peptide represented by the following formula (24)

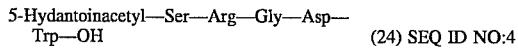
5-Hydantoinacetyl—Ser—Arg—Gly—Asp—Trp—OH (24) SEQ ID NO:4

The titled peptide (40 mg) was synthesized by the same procedure as in Example 1.
Amino acid analysis (6N HCl+phenol, 24 hr, 110° C.)
Asp 1.19 (1)
Ser 1.00 (1)
Gly 1.26 (1)
Trp—(1)
Arg 1.13 (1)
HPLC analysis A spectrum of analytical HPLC using Cosmosil 5C18-AR (ø4.6× 200 mm) column at a flow rate of 1.0 ml/min by elution in a gradient of acetonitrile of 10–40% (60 min) in 0.1% TFA indicated a single peak at a retention time of 16.0 minutes.
FAB-MS: M+H Calculated 760.3, Found 760

[Example 20]

Synthesis of the peptide represented by the following formula (25)

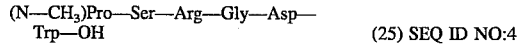
(N—CH$_3$)Pro—Ser—Arg—Gly—Asp—Trp—OH (25) SEQ ID NO:4

The titled peptide (40 mg) was synthesized by the same procedure as in Example 16.
Amino acid analysis (6N HCl+phenol, 24 hr, 110° C.)
Asp 0.84 (1)
Ser 1.00 (1)
Gly 1.16 (1)
Trp—(1)
Arg 1.11 (1)
HPLC analysis A spectrum of analytical HPLC using Cosmosil 5C18-AR (ø4.6× 200 mm) column at a flow rate of 1.0 ml/min by elution in a gradient of acetonitrile of 10–40% (60 min) in 0.1% TFA indicated a single peak at a retention time of 21.0 minutes.
FAB-MS: M+H Calculated 731.3, Found 731

[Example 21]

Synthesis of the peptide represented by the following formula (26)

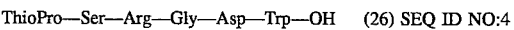
ThioPro—Ser—Arg—Gly—Asp—Trp—OH (26) SEQ ID NO:4

The titled peptide (40 mg) was synthesized by the same procedure as in Example 16.
Amino acid analysis (6N HCl+phenol, 24 hr, 110° C.)
Asp 0.84 (1)
Ser 1.00 (1)
Gly 1.16 (1)
Trp—(1)
Arg 1.11 (1)
HPLC analysis A spectrum of analytical HPLC using Cosmosil 5C18-AR (ø4.6× 200 mm) column at a flow rate of 1.0 ml/min by elution in a gradient of acetonitrile of 10–40% (60 min) in 0.1% TFA indicated a single peak at a retention time of 20.0 minutes.
FAB-MS: M+H Calculated 735.3, Found 735

[Example 22]

Synthesis of the peptide represented by the following formula (27)

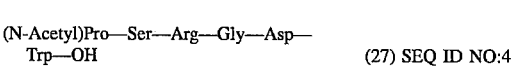
(N-Acetyl)Pro—Ser—Arg—Gly—Asp—Trp—OH (27) SEQ ID NO:4

The titled peptide (40 mg) was synthesized by the same procedure as n Example 16.
Amino acid analysis (6N HCl+phenol, 24 hr, 110° C.)
Asp 0.90 (1)
Ser 1.00 (1)
Gly 1.17 (1)
Trp—(1)
Arg 1.10 (1)
Pro 1.00 (1)
HPLC analysis A spectrum of analytical HPLC using Cosmosil 5C18-AR (ø4.6× 200 mm) column at a flow rate of 1.0 ml/min by elution in a gradient of acetonitrile of 10–40% (60 min) in 0.1% TFA indicated a single peak at a retention time of 22.0 minutes.
FAB-MS: M+H Calculated 759.3, Found 759

[Example 23]

Synthesis of the peptide represented by the following formula (28)

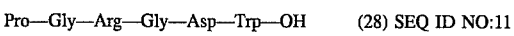
Pro—Gly—Arg—Gly—Asp—Trp—OH (28) SEQ ID NO:11

The titled peptide (40 mg) was synthesized by the same procedure as in Example 16.
Amino acid analysis (6N HCl+phenol, 24 hr, 110° C.)
Asp 0.84 (1)
Gly 1.96 (2)
Trp—(1)
Arg 1.06 (1)
Pro 1.00 (1)
HPLC analysis A spectrum of analytical HPLC using Cosmosil 5C18-AR (ø4.6× 200 mm) column at a flow rate of 1.0 ml/min by elution in a gradient of acetonitrile of 10–40% (60 min) in 0.1% TFA indicated a single peak at a retention time of 20.0 minutes.
FAB-MS: M+H Calculated 687.3, Found 687

23

[Example 24]

Synthesis of the peptide represented by the following formula (29)

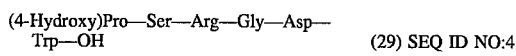
(4-Hydroxy)Pro—Ser—Arg—Gly—Asp—Trp—OH  (29) SEQ ID NO:4

The titled peptide (40 mg) was synthesized by the same procedure as in Example 16.
Amino acid analysis (6N HCl+phenol, 24 hr, 110° C.)

Asp 0.88 (1)
Ser 0.93 (1)
Gly 1.04 (1)
Trp—(1)
Arg 1.00 (1)

HPLC analysis

A spectrum of analytical HPLC using Cosmosil 5C18-AR (∅4.6× 200 mm) column at a flow rate of 1.0 ml/min by elution in a gradient of acetonitrile of 10–40% (60 min) in 0.1% TFA indicated a single peak at a retention time of 17.0 minutes.

FAB-MS: M+H Calculated 733.3, Found 733

[Example 25]

Synthesis of the peptide represented by the following formula (30)

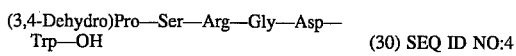
(3,4-Dehydro)Pro—Ser—Arg—Gly—Asp—Trp—OH  (30) SEQ ID NO:4

The titled peptide (40 mg) was synthesized by the same procedure as in Example 16.
Amino acid analysis (6N HCl+phenol, 24 hr, 110° C.)

Asp 0.94 (1)
Ser 0.94 (1)
Gly 1.06 (1)
Trp—(1)
Arg 1.00 (1)

HPLC analysis

A spectrum of analytical HPLC using Cosmosil 5C18-AR (∅4.6× 200 mm) column at a flow rate of 1.0 ml/min by elution in a gradient of acetonitrile of 10–40% (60 min) in 0.1% TFA indicated a single peak at a retention time of 20.0 minutes.

FAB-MS: M+H Calculated 715.3, Found 715

[Example 26]

Synthesis of the peptide represented by the following formula (31)

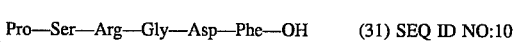
Pro—Ser—Arg—Gly—Asp—Phe—OH  (31) SEQ ID NO:10

The titled peptide (40 mg) was synthesized by the same procedure as in Example 16.
Amino acid analysis (6N HCl+phenol, 24 hr, 110° C.)

Asp 1.04 (1)
Ser 0.90 (1)
Gly 1.04 (1)
Phe 1.03 (1)
Arg 1.00 (1)
Pro 1.08 (1)

HPLC analysis

A spectrum of analytical HPLC using Cosmosil 5C18-AR (∅4.6× 200 mm) column at a flow rate of 1.0 ml/min by elution in a gradient of acetonitrile of 10–40% (60 min) in 0.1% TFA indicated a single peak at a retention time of 17.0 minutes.

FAB-MS: M+H Calculated 678.3, Found 678

[Example 27]

Synthesis of the peptide represented by the following formula (32)

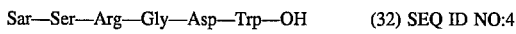
Sar—Ser—Arg—Gly—Asp—Trp—OH  (32) SEQ ID NO:4

The titled peptide (40 mg) was synthesized by the same procedure as in Example 16.
Amino acid analysis (6N HCl+phenol, 24 hr, 110° C.)

Asp 0.87 (1)
Ser 1.00 (1)
Gly 1.14 (1)
Trp—(1)
Arg 1.04 (1)

HPLC analysis

A spectrum of analytical HPLC using Cosmosil 5C18-AR (∅4.6× 200 mm) column at a flow rate of 1.0 ml/min by elution in a gradient of acetonitrile of 10–40% (60 min) in 0.1% TFA indicated a single peak at a retention time of 17.5 minutes.

FAB-MS: M+H Calculated 691.3, Found 691

[Experimental Example 1] Platelet Aggregation-Inhibiting Ability of the Compounds of the Present Invention Measurement of Activity in the Synthetic Peptide ① Measurement of in vitro Human Platelet Aggregation using PRP Healthy male volanteers who had not taken any medicines for at least two weeks were treated as subjects. Blood was collected from the forearm vein of each subject on an empty stomach using a plastic syringe in which 1/10 volume of a 3.8% sodium citrate solution had been preliminarily charged and which was equipped with a #19 needle. Immediately after the blood collection, the syringe was stirred gently to mix the blood with the sodium citrate solution. The mixed blood was centrifuged (1100 rpm, 250 g) at room temperature for 15 minutes and the rotation was stopped without applying the brake. Then, the supernatant was collected with a Komagome type pipette to obtain platelet-rich plasma (PRP). The PRP was stored at room temperature. The blood remaining after centrifuging was further centrifuged (3500 rpm, 1500 g) at room temperature for 15 minutes and the rotation was stopped without applying the brake. The supernatant was collected to obtain platelet-poor plasma (PPP). After the preparation of the PRP, the number of platelets was counted and samples containing more than $2\times10^8$/ml of platelets were used for the following experiments.

Platelet aggregation was measured using an 8-channel platelet aggregation measuring instrument (Hematracer, Nikoh Bioscience, Tokyo, Japan) on the basis of the change in light transmittance through PRP. First, PPP and PRP (each 200 µl) were placed in glass cuvettes and incubated at 37° C. Thereafter, the transmittance was measured. The transmittance of PPP was determined as 100% and that of PRP as 0%. Then, 10 µl of saline or a sample-containing saline was added to PRP and incubated at 37° C. for one minute. A collagen solution (10 µl) at a concentration of 100 µg/ml was added (final concentration: 5 µg/ml) to induce aggregation and thereafter the transmittance was measured over 7 minutes. The experiment was carried out using those samples in which aggregation with collagen and ADP was confirmed in the first step and in which the maximum rate of the aggregation with collagen was at least 70%.

The sample was dissolved in saline at a concentration of $2.2\times 10^{-2}$M and a 2-fold dilution series was prepared for use in the experiments. The samples insoluble in saline were dissolved in saline containing 10% DMSO (Dimethyl sulfoxide).

The results were calculated as follows:

$$\text{Percent aggregation inhibition} = \left[1 - \frac{\text{Maximum percent aggregation when the sample is added}}{\text{Maximum percent aggregation when saline is added}}\right] \times 100 \quad \text{Calculation Formula (1)}$$

A graph was constructed by plotting the percent aggregation inhibition against sample concentration and from the graph, the concentration at which the aggregation is inhibited by 50% ($IC_{50}$) was calculated. $IC_{50}$ of each sample is shown in Table 2.

the stability in whole blood. Futhermore, the mixed blood was centrifuged (800 g) for 10 minutes and the rotation was stopped without applying the brake. Then, the supernatant was collected to obtain a plasma fraction. This plasma fraction was examined for the stability in plasma.

The whole blood or plasma (225 μl) was placed in a test tube and heated to 37° C. Each of the synthetic peptides was dissolved in saline (pH 7.4) to prepare a solution at a concentration of 1 mM. Each of the synthetic peptide solutions was added to the whole blood or plasma in an amount of 25 μl (final concentration: 100 μM) and incubated for a certain period of time. After the incubation, the solution

TABLE 2

Platelet Aggregation-Inhibiting Activity of the Peptides of the Present Invention

| Peptide | $IC_{50}$ |
| --- | --- |
| Trp—Ser—Arg—Gly—Asp—Trp—OH | (Example 1) $6.3 \times 10^{-6}$ M SEQ ID NO: 2 |
| Trp—Val—Arg—Gly—Asp—Trp—OH | (Example 2) $8.3 \times 10^{-6}$ M SEQ ID NO: 3 |
| $CH_3CO$—Trp—Ser—Arg—Gly—Asp—Trp—$NH_2$ | (Example 3) $1.0 \times 10^{-5}$ M SEQ ID NO: 4 |
| 5-Methoxyindole-3-acetyl-Ser—Arg—Gly—Asp—Trp—OH | (Example 4) $1.1 \times 10^{-5}$ M SEQ ID NO: 4 |
| 2-Methyindole-3-acetyl-Ser—Arg—Gly—Asp—Trp—OH | (Example 5) $2.2 \times 10^{-5}$ M SEQ ID NO: 4 |
| Indole—3—butanoyl—Ser—Arg—Gly—Asp—Trp—OH | (Example 6) $2.7 \times 10^{-5}$ M SEQ ID NO: 5 |
| Indole-3-acetyl-Ser—Arg—Gly—Asp—Trp—OH | (Example 7) $2.1 \times 10^{-5}$ M SEQ ID NO: 5 |
| Phe—Ser—Arg—Gly—Asp—Phe—OH | (Example 8) $6.7 \times 10^{-5}$ M SEQ ID NO: 6 |
| Orotyl-Ser—Arg—Gly—Asp—Trp—OH | (Example 9) $4.0 \times 10^{-6}$ M SEQ ID NO: 5 |
| Hydoorotyl-Ser—Arg—Gly—Asp—Trp—OH | (Example 10) $8.7 \times 10^{-6}$ M SEQ ID NO: 5 |
| Pyroglutamyl-Ser—Arg—Gly—Asp—Trp—OH | (Example 11) $5.7 \times 10^{-6}$ M SEQ ID NO: 4 |
| Trp—Ala—Arg—Gly—Asp—Trp—OH | (Example 12) $3.1 \times 10^{-5}$ M SEQ ID NO: 7 |
| Trp-β Ala—Arg—Gly—Asp—Trp—OH | (Example 13) $1.2 \times 10^{-5}$ M SEQ ID NO: 8 |
| Trp—Gly—Arg—Gly—Asp—Trp—OH | (Example 14) $2.2 \times 10^{-5}$ M SEQ ID NO: 9 |
| 2-Oxo-4-thiazolidine carboxyl-Ser—Arg—Gly—Asp—Trp—OH | (Example 15) $2.8 \times 10^{-5}$ M SEQ ID NO: 4 |
| Pro—Ser—Arg—Gly—Asp—Trp—OH | (Example 16) $8.7 \times 10^{-7}$ M SEQ ID NO: 10 |
| (L-2-Azetidinecarboxyl)-Ser—Arg—Gly—Asp—Trp—OH | (Example 17) $1.3 \times 10^{-6}$ M SEQ ID NO: 4 |
| (L-Pipecolinyl)-Ser—Arg—Gly—Asp—Trp—OH | (Example 18) $1.1 \times 10^{-5}$ M SEQ ID NO: 4 |
| 5-Hydantoinacetyl-Ser—Arg—Gly—Asp—Trp—OH | (Example 19) $6.9 \times 10^{-6}$ M SEQ ID NO: 4 |
| (N—$CH_3$)Pro—Ser—Arg—Gly—Asp—Trp—OH | (Example 20) $1.1 \times 10^{-5}$ M SEQ ID NO: 4 |
| Thiopro-Ser—Arg—Gly—Asp—Trp—OH | (Example 21) $2.8 \times 10^{-5}$ M SEQ ID NO: 4 |
| (N-Acetyl)Pro—Ser—Arg—Gly—Asp—Trp—OH | (Example 22) $1.3 \times 10^{-5}$ M SEQ ID NO: 4 |
| Pro—Gly—Arg—Gly—Asp—Trp—OH | (Example 23) $5.5 \times 10^{-6}$ M SEQ ID NO: 11 |
| (4-Hydroxy)Pro—Ser—Arg—Gly—Asp—Trp—OH | (Example 24) $2.7 \times 10^{-5}$ M SEQ ID NO: 4 |
| (3,4-Dehydro)Pro—Ser—Arg—Gly—Asp—Trp—OH | (Example 25) $1.6 \times 10^{-6}$ M SEQ ID NO: 4 |
| Pro—Ser—Arg—Gly—Asp—Phe—OH | (Example 26) $1.6 \times 10^{-6}$ M SEQ ID NO: 10 |
| Ser—Ser—Arg—Gly—Asp—Trp—OH | (Example 27) $3.5 \times 10^{-6}$ M SEQ ID NO: 4 |
| Arg—Gly—Asp—Ser—OH | (Comparative Example 1) $4.0 \times 10^{-4}$ M SEQ ID NO: 12 |

Table 2 shows that the introduction of a molecule having a hydrophobic group such as Trp at the both ends of RGD sequence increases the platelet aggregation-inhibiting activity greatly compared to the amino acid sequence RGDS which is present in the fibrinogen molecule (Table 2, Comparative Example 1). It was verified that the platelet aggregation-inhibiting ability of the peptides of the present invention is remarkably improved compared to that of the amino acid sequence RGDS-OH (purchased from Peptide Laboratory, Minoo-shi, Japan) that is listed as Comparative Example in Table 2 and which is contained in the fibrinogen molecule.

[Experimental Example 2] Stability of the Synthetic Peptides in Plasma and in the Body of an Organism
(1) Evaluation of Stability in Whole Blood and in Plasma
[Method]

Healthy male volanteers who had not taken any medicines for at least two weeks were treated as subjects. Blood was collected from the forearm vein of each subject on an empty stomach using a plastic syringe in which ¹/₁₀ volume of a 3.8% sodium citrate solution had been preliminarily charged. Immediately after the blood collection, the syringe was stirred gently to mix the blood with the sodium citrate solution. The blood sample thus prepared was examined for was cooled with ice to stop the degradation reaction. The plasma was stored frozen at −20° C. without performing any treatments. The whole blood was centrifuged at 2000 g for 5 minutes at 4° C. and the supernatant was stored frozen.

The samples were analyzed by reversed phase HPLC. The peak area of each synthetic peptide was calculated and the stability in the whole blood or plasma was evaluated from the change of the peak area.

Figure 2:
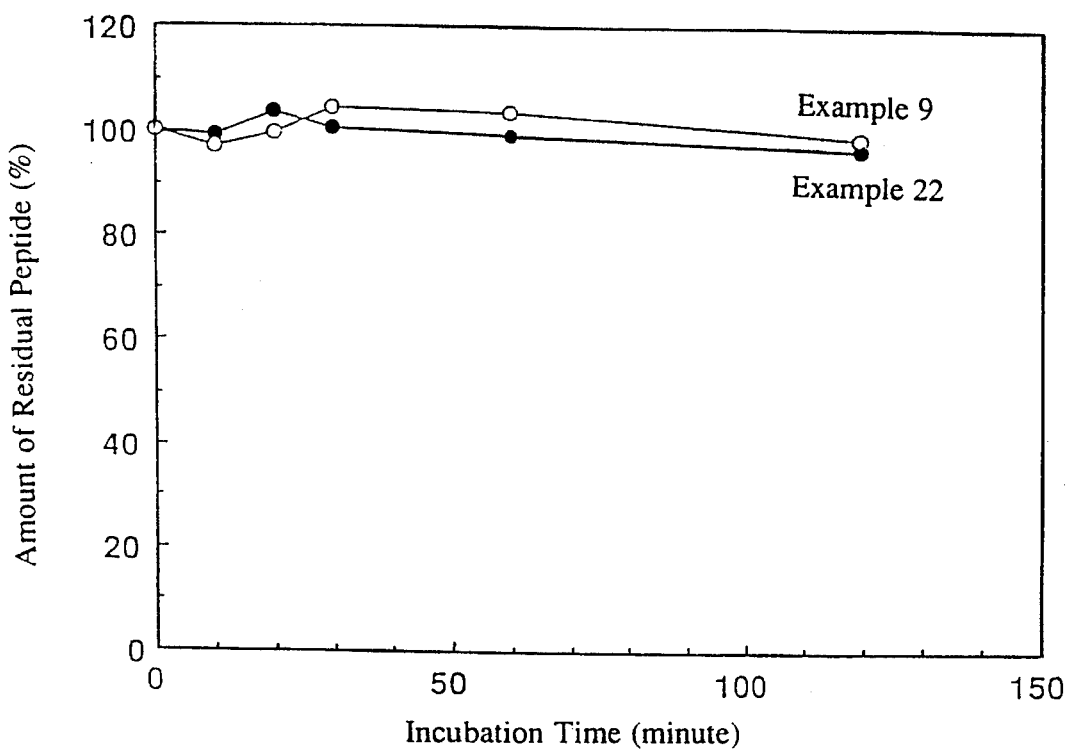
FIG. 2 is another graph showing the stability of synthetic peptides in human plasma.
Figure 3:
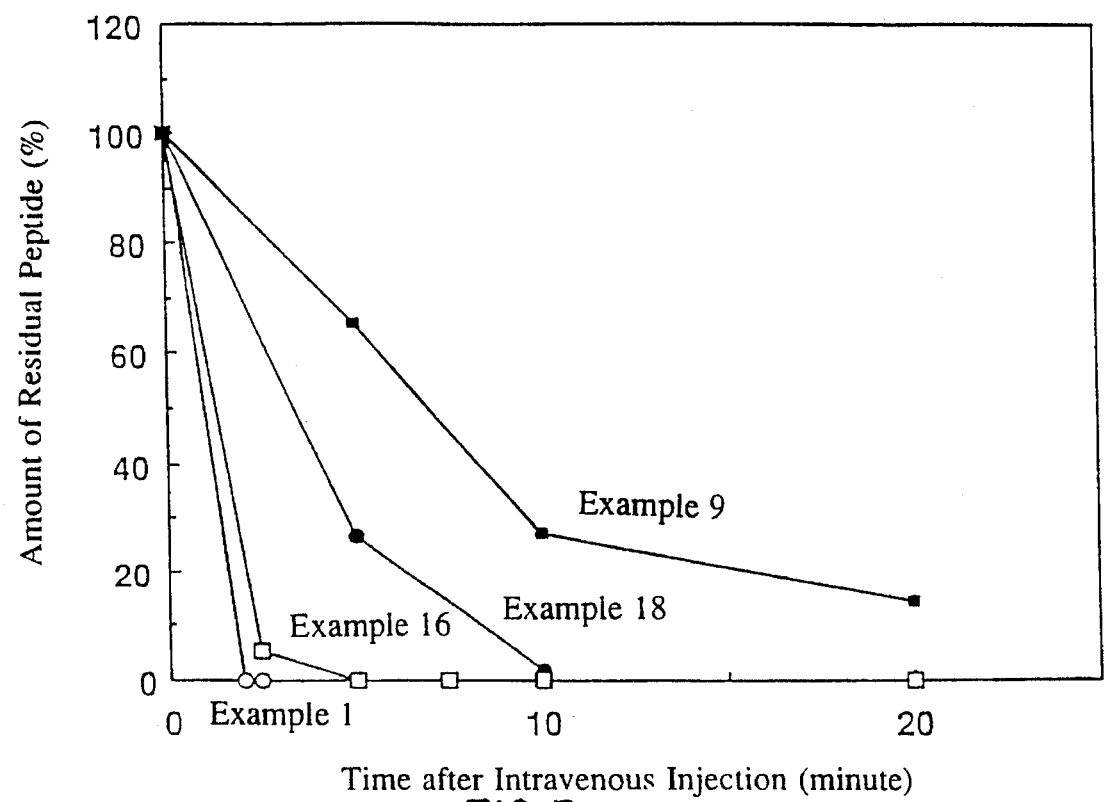
FIG. 3 is a graph showing the stability of synthetic peptides in mice.

FIGS. 1–3 show the stability in plasma of the peptides or their analogues represented by the general formula:

A—Ser—Arg—Gly—Asp—Trp—OH    SEQ ID NO:4 wherein A is an amino acid or its derivative, a vitamin, a vitamin-like active substance or its derivative, or a base of nucleic acids or its derivative.

Table 3 is a summary of their half-time.

TABLE 3

Stability of the Synthetic Peptides in Human Plasma
Half-Time of the Synthetic Peptides in Plasma

| Synthetic Peptide | Half-Time |
|---|---|
| Example 9 | ≧240 minutes |
| Example 18 | ≧120 minutes |
| Example 16 | 74.5 minutes |
| Example 1 | 11.5 minutes |
| Example 11 | ≧240 minutes |

When A is a naturally occurring amino acid tryptophan having a primary amino group, the peptide was broken down at a very high rate and its half-time was 11.5 minutes. In contrast, when A is a naturally occurring amino acid proline having a secondary amino group (imino group), the peptide was more stable in plasma than the peptide containing proline and its half-time was 74.5 minutes. On the other hand, if the peptide is a proline derivative having the same secondary amino group (imino group), its stability in plasma varied greatly depending on the number of carbon atoms in a hetero ring or the presence or absence of a side chain. The compound in which azetidinecarboxylic acid having a 4-membered heterocyclic structure was introduced had a half-time of 49 minutes and it was more degradable in plasma than the compound in which proline having a 5-membered heterocyclic structure was introduced. In contrast, the compound in which pipecolic acid having a 6-membered heterocyclic structure was introduced had a half-time of at least 120 minutes in plasma and it was very stable.

On the other hand, the compounds in which A is an amino acid, a nucleic acid or a vitamin derivative that have a carbonyl group in a heterocyclic structure, such as orotic acid, pyroglutamic acid and the like were all extremely stable in plasma and their half-times were at least 240 minutes.

The stability in whole blood showed the same tendency as that in plasma. No difference in half-time could be recognized between whole blood and plasma.

As shown above, the compounds having different degrees of stability in plasma can be obtained by varying the compounds to be introduced at the both ends of the synthetic peptide. It is meaningful that the compounds having different degrees of stability in blood can be properly used in the application to blood coagulation-inhibiting agents for extracorporeal circulation depending on the kind of extracorporeal circulation system used, such as an artificial dialyzator, an artificial heart and lung, and the like, bleeding amount during surgical operations, and the like and it is also meaningful that an optimum compound can be selected depending on the purpose of its application.

(2) Evaluation of in vivo Stability
[Method]

For the evaluation of stability, MCH (ICR) strain mice (male, body weight: 28–32 g) were used. The synthetic peptides were dissolved in sterilized saline at concentrations of 10–20 mM to prepare sample solutions. Each sample solution was injected intravenously from the tail vein in an amount of 0.15 ml per mouse (peptide amount: 1–2 mg/mouse). After a certain period of time, blood was collected from the abdominal vein using an injection syringe treated with heparin. Immediately after the collection, the blood was centrifuged (1500 g, 3 minutes) at 4° C. and the supernatant was stored frozen at −20° C. Each of the supernatants was analyzed by reversed phase HPLC in the same manner as that in the aforementioned evaluation of stability in plasma.

FIG. 3 and Table 4 show the in vivo stability of the peptides or their analogues represented by the general formula:

A—Ser—Arg—Gly—Asp—Trp—OH        SEQ ID NO:4 wherein A is an amino acid or its derivative, a vitamin, a vitamin-like active substance or its derivative, or a base of nucleic acids or its derivative.

TABLE 4 in vivo Stability of the Synthetic Peptides in Mice
Half-Time of the Synthetic Peptides in Mice

| Synthetic Peptide | Half-Time |
|---|---|
| Example 9 | 10.1 minutes |
| Example 18 | 3.3 minutes |
| Example 16 | ≦2 minutes |
| Example 1 | ≦2 minutes |

The compounds in which A is a naturally occurring L-amino acid such as tryptophan, proline and the like were characterized by high in vivo degradability and they were almost completely broken down within the period from the intravenous injection to the blood collection (half-time in the body of a mouse: ≦2 minutes). In contrast, the compound in which azetidinecarboxylic acid (a proline analogue) was introduced had a half-time of 3.3 minutes and the compound in which orotic acid (a vitamin-like active substance) was introduced had a half-time of 6.9 minutes. These compounds were somewhat more degradable than the compounds in which the naturally occurring L-amino acids were introduced.

Thus, the peptide compounds represented by the above general formula are generally characterized by high in vivo degradability. This is a highly significant point considering the application of the peptides of the present invention to blood coagulation-inhibiting agents for extracorporeal circulation. Stated more specifically, these compounds have half-times of from several minutes to several hours and inhibit the platelet aggregation during the extracorporeal circulation but, on the other hand, they are broken down within several minutes after blood returns to the body. In other words, these compounds have an extremely important property in that they exhibit the anti-thrombogenic activity in an extracorporeal circulation system but that they do not prolong the time required to inhibit bleeding in the body.

[Experimental Example 3] Applicability of the Peptides of the Present Invention to Blood Coagulation-Inhibiting Agents for Extracorporeal Circulation (1) In order to examine how long the peptides of the present invention and heparin, which is used as an anticoagulant at present, can remain without being broken down or eliminated and how long the activity of them persists, intravenous injection experiments were carried out using beagles.

Since the peptides of the present invention have the platelet aggregation-inhibiting activity, the amount of the peptides which remain in the body of an organism without being broken down can be determined by collecting blood and measuring the platelet aggregation-inhibiting activity of the blood at given intervals of time. Thus, the in vivo stability of the peptides can be estimated.

In the experiments, a male beagle having a body weight of 10 Kg was used. The peptide prepared in Example 9 was dissolved in saline and injected into the dog through the superior cutaneous vein using an injection syringe equipped with a 21 G needle. Before injection and 5, 15, 30, 60, 120 180 and 360 minutes after injection, blood was collected from the beagle without anesthetization through the superior cutaneous vein using an extension tube equipped with a 21 G needle under spontaneous bleeding and the collected blood was mixed with a 3.8% sodium citrate solution at a volume ratio of 9 (whole blood) to 1 (sodium citrate solution). The collected blood was centrifuged at 1000 rpm for 10 minutes to prepare platelet-rich plasma (PRP). The reminder was further centrifuged at 3000 rpm for 15 minutes to prepare platelet-poor plasma (PPP).

The platelet aggregation ability was determined by measuring the platelet aggregation of the PRP with collagen and ADP using an aggregometer. In the measurement, ADP was added at a final concentration of 7.5 and 10.0 µM and collagen was added at a final concentration of 7.5 and 10.0 µg/ml.

Figure 4A:
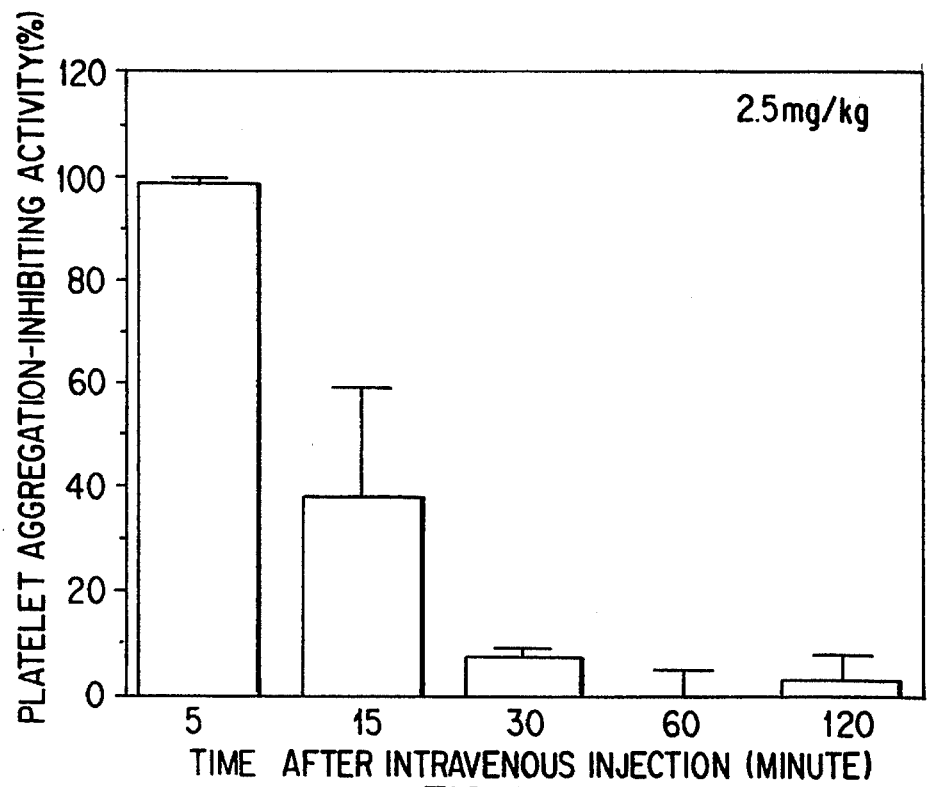
FIG. 4 is a graph showing platelet aggregation-inhibiting activity versus prothrombin time in an experiment using a beagle.

FIG. 4A shows the time course of recovery of the platelet aggregation activity when the peptide prepared in Example 9 was injected into the beagle in an amount of 5 mg/Kg. Collagen (10 µg/ml) was used as an inducer. The platelet aggregation was completely inhibited 5 minutes after the injection but the platelet aggregation activity was recovered with the passage of time and after 45–60 minutes, it completely recovered to the level before the injection. Even in the case where the concentration of collagen was changed or ADP was used as an inducer, the same results were obtained. These results show that the peptide was broken down in the body or eliminated from the kidney out of the body within 60 minutes and that the blood level of the peptide was lowered accordingly.

(2) Heparin, currently used as an anticoagulant, was used as a comparison with the peptides of the present invention.

Since heparin does not act on platelets, its in vivo stability can not be determined by the method described in (1). Therefore, the in vivo stability of heparin was estimated by measuring the time-dependent change in the anticoagulation action which is the main action of heparin.

In the experiments, haparin as dissolved in saline was injected into the vein and blood was collected at given intervals of time to prepare PPP by the same method as that described in (1).

In the measurement of the anticoagulation action, the prepared PPP was used to measure prothrombin time, which is an indicator of blood coagulation activity in vitro, and activated partial thromboplastin time according to a conventional method. Each measurement was conducted under preincubation conditions at 37° C. for 3 minutes using AMELUNG KC-10A (Baxtor CO.). The rate of the disappearance of heparin from the body can be estimated by measuring the prolongations of the prothrombin time and the activated partial thromboplastin time (i.e., the prolongation of time up to coagulation) after the injection.

Figure 4B:
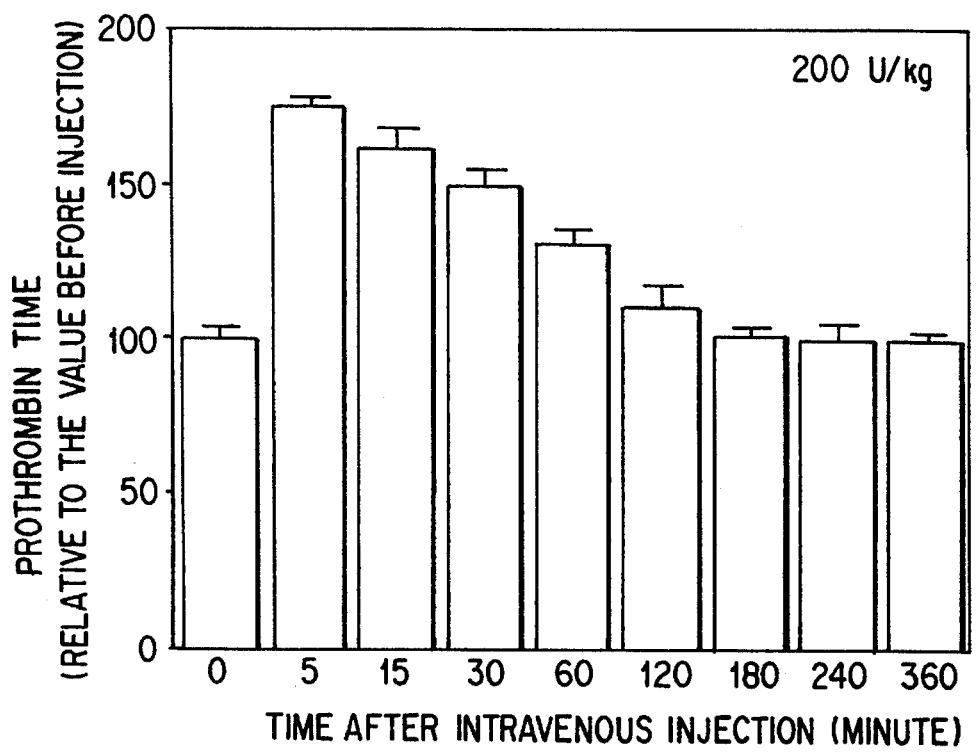

FIG. 4B shows the time-dependent change in the prolongation tendency of the prothrombin time when heparin was injected intravenously into the beagle in an amount of 200 U/Kg. Immediately after the injection of heparin, the prothrombin time prolonged 1.5 to 2.0 folds from the value before injection. It gradually recovered to the level before injection with the passage of time. It required 2–3 hours to completely recover to the level before injection. The same results were obtained with respect to the activated partial thromboplastin time. These results show that heparin is broken down in vivo or eliminated from the body at a slow rate and thereby its activity was retained for several hours.

As shown above, the activity of the peptide prepared in Example 9 disappeared rapidly compared to heparin which has been used as an anticoagulant in an extracorporeal circulation in the prior art. This verifies that the peptides do not have the disadvantage of heparin that hemorrhagic tendency continues for several hours after the end of the application of an extracorporeal circulation system such as an artificial dialyzator and that the peptides can reasonably be expected to replace heparin as new blood coagulation-inhibiting agents.

(3) Experiment on an Extracorporeal Circulation Model Using a Beagle

In order to confirm that the peptides of the present invention have the action of inhibiting blood coagulation in an extracorporeal circulation system, experiments were carried out on an artificial dialysis model using a beagle which is one of extracorporeal circulation models (see Hamano et al., Thromb. Res. 55 (1989) 438–449).

Figure 5:
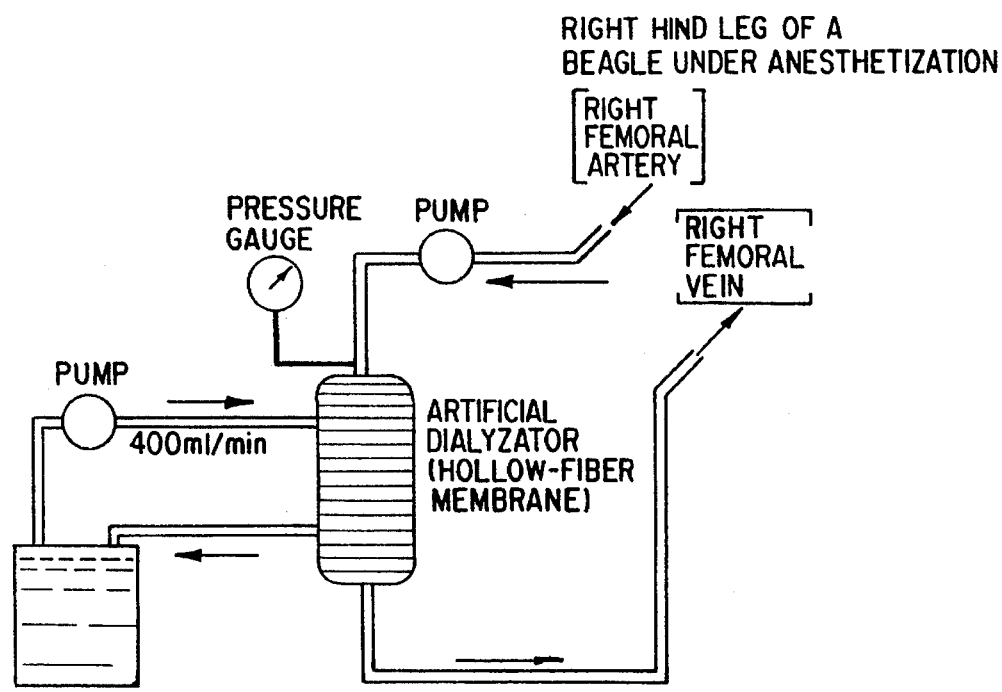
FIG. 5 is a scheme of a dialysis circuit in a dog artificial dialysis model.

In the experiments, beagles weighing about 10–12 Kg were used. The beagles were anesthetized with pentobarbital (about 30 mg/Kg) and the right hind leg was incised to expose the femoral artery and femoral vein. Cannulas were inserted into the exposed femoral artery and femoral vein and connected to the artificial dialyzator for experiments (Kuraray, Osaka, Japan) having a circuit configuration as shown in FIG. 5. A hollow-fiber dialyzer (RENAK-A, RA-04, 0.4 $m^2$, Kawasumi Laboratories, Tokyo) was used. A pump for blood was placed between the femoral artery and the dialyzator and operated to keep the blood flow rate at 25 ml/min in the extracorporeal circulation system during the experiments.

The following three parameters were measured in the experiments: ① the pressure in the up-stream portion of the dialyzer (perfusion pressure), ② the percent platelet adhesion and ③ the whole blood coagulation time. The pressure under ① was measured by a pressure gauge incorporated in the upper stream portion of the dialyzator in the dialysis circuit as shown in FIG. 5. Since at the site of dialyzer blood often experiences contacts with foreign materials and blood flows in a narrow space, blood coagulation is most likely to occur at this site in the dialysis circuit. If blood coagulation occurs there, the dialyzer is clogged and the blood pressure in the up-stream portion will increase. The change in the perfusion pressure at this site indicates the degree of blood coagulation in the dialysis circuit. In connection with parameters ② and ③, an aliquot of blood was sampled at the inlet and outlet of the dialysis part at given intervals of time to measure ② and ③ by conventional methods. Parameters ② and ③ indicate how the function of platelets and that of blood coagulation (the degree of activation), respectively, change with the progress of the experiments.

The experiments began with a continuous injection of a solution of the peptide of the present invention in saline from the arterial side (or the inlet side of the dialysis circuit) immediately after the circuit set-up. The amount of injection was 10 mg/dog or 30 mg/dog and the total amount was gradually injected over 1 hour (injection rate: 1 ml/min). In a control, only saline was continuously injected in the same manner. The injection of the drug was stopped after 60 minutes and blood was thereafter circulated up to 180 minutes to continue the measurement of the above parameters. When the pressure exceeded 500 mmHg, the experiment was stopped at that time.

Figure 6:
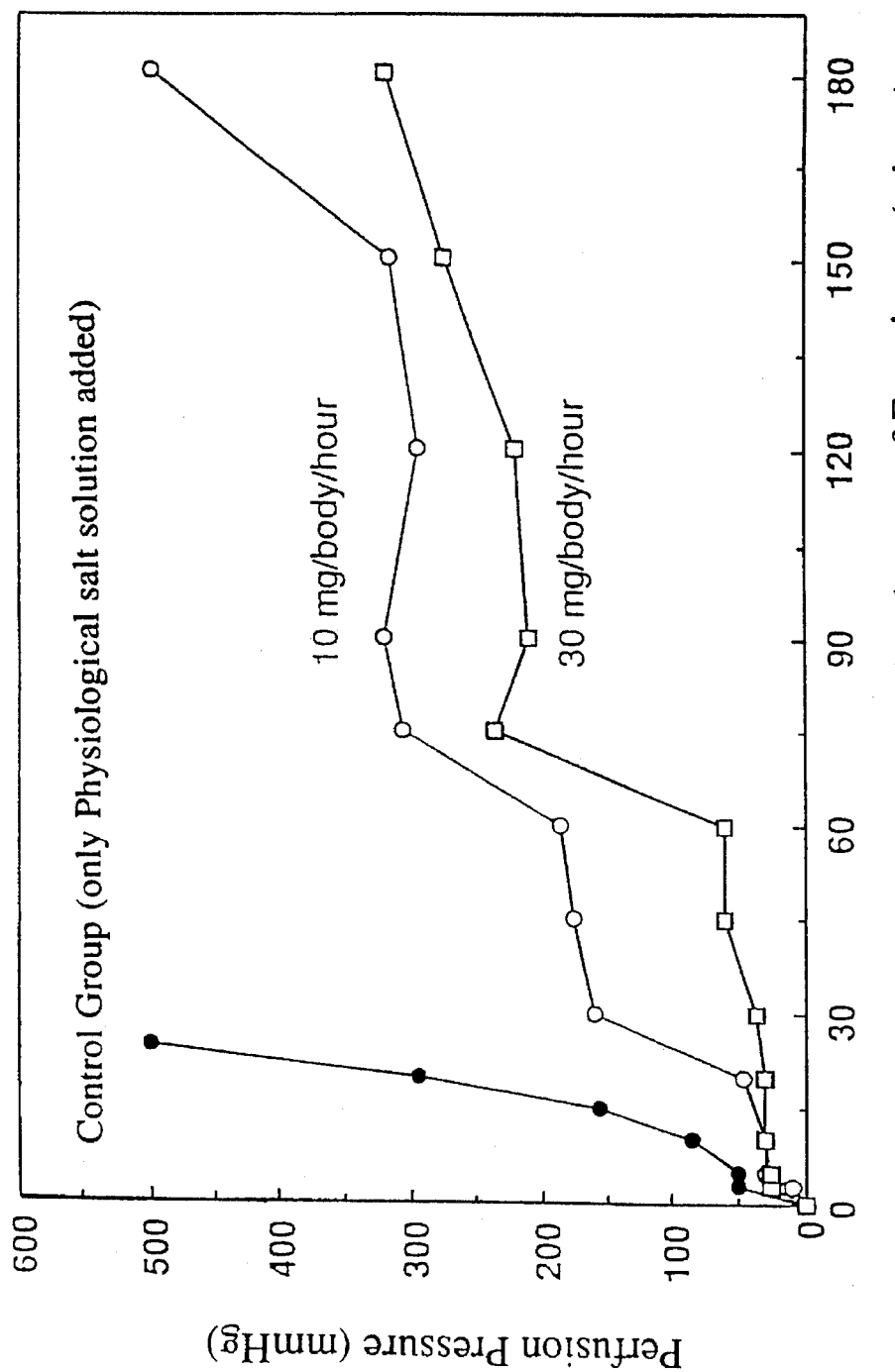
FIG. 6 is a graph showing blood coagulation-inhibiting effect in a dog artificial dialysis model.

FIG. 6 shows the results of the experiments in which the inhibitory effect of the compound of Example 9 on the increase in the perfusion pressure was examined. The numbers on the abscissa indicate time after the beginning of the drug injection and those on the ordinate indicate the perfusion pressure. The perfusion pressure was 0 mmHg right after the circuit set-up and increased due to the occurrence of blood coagulation. In the control group into which only saline was injected, the perfusion pressure increased rapidly after 10 minutes and exceeded 500 mmHg in 25 minutes, making further measurements impossible. As shown in this case, when no drug was injected, blood coagulation occurred rapidly in the dialysis circuit, particularly at the site of the dialyzer. In contrast, when the peptide of the present invention prepared in Example 9 was injected, blood coagulation was obviously inhibited. When the amount of injection of the drug was 10 mg/dog, the increase rate of the perfusion pressure was evidently slow and this effect continued after the completion of the injection. When the amount of injection of the drug was increased to 30 mg/dog, little or no increase in the perfusion pressure was observed during the injection of the drug.

With respect to the platelet aggregation ability and the whole blood coagulation time, changes almost parallel to the increase pattern of the perfusion pressure were observed (not shown in Figures). Briefly, in the control group, the increase in the platelet aggregation ability and the decrease in the whole blood coagulation time were observed with the passage of time. This indicated that the platelets were activated and thereby the blood coagulation system was activated and that as a result, the dog was under such conditions that blood coagulation was highly likely to occur. In contrast, in the group into which the peptide of the present invention (Example 9) was injected, it was revealed that the blood coagulation ability dropped to approximately 0% during the continuous injection of the drug and that, therefore, the dog was under such conditions that the platelet activity was completely inhibited. In addition, the whole blood coagulation time was significantly prolonged during this period.

As shown above, the peptides of the present invention inhibited completely the blood coagulation in an extrecorporeal circulation system. This indicates that the peptides of the present invention can satisfactorily be used as a substitute for currently used heparin. As described above, although heparin inhibits completely the blood coagulation in an extracorporeal system but, at the same time, it has the disadvantage that it is eliminated from the body at a slow rate and thereby inhibits blood coagulation while promoting hemorrhagic tendency for several hours even after the detachment of the system. In these points, the peptides of the present invention are different from heparin as shown in FIG. 4. Namely, the peptide of the present invention has the advantage that it is highly degradable in the body and that therefore, if its injection is stopped, blood coagulation will soon recover to the normal level before drug injection. Futhermore, since the peptides of the present invention are extremely low in toxicity, they are promising as new blood coagulation-inhibiting agents that compensate for the disadvantages of heparin.

As shown above, if the peptides of the present invention are dissolved in saline or a citric acid solution and if they are injected continuously at a rate of approximately 3 mg/hour/kg from the inlet of an extrecorporeal circulation system by means of drop infusion and the like, satisfactory blood coagulation-inhibiting action can be expected. It is believed that in the actual application to humans, the dose can be further reduced.

If the peptides of the present invention are combined with other coagulants having entirely different modes of action such as a citric acid solution, heparin, futhan, a fibrinolytic agent and the like, synergism can be expected. Therefore, the dose of both drugs can be reduced and greater safety is insured.

[Experimental Example 4] Applicability of the Peptides of the Present Invention to Agents for Protecting Platelet Preparations for Blood Transfusion Healthy male volunteers who had not taken any medicines for at least two weeks were treated as subjects. Blood was collected from the hypogastric vein of each subject on an empty stomach using a syringe in which the synthetic peptide dissolved at a concentration ten times the intended final concentration in a 3.8% sodium citrate solution had been preliminarily charged in a ¹/₁₀ volume and which was equipped with a #19 needle. Immediately after the blood collection, the syringe was stirred gently to mix the blood with the sodium citrate solution. The mixed blood was centrifuged (1100 rpm, 250 g) at room temperature for 15 minutes and the rotation was stopped without applying the brake. Then, the supernatant was collected with a pipette to obtain a platelet fraction. The remaining blood was further centrifuged (3000 rpm, 1000 g). The supernatant was collected to obtain platelet-poor plasma and stored.

The platelet fraction was placed in a polypropylene test tube, which was capped with a membrane filter to ensure breathability. Then, the test tube was placed on a shaker and stored at room temperature while shaking through vibrational amplitude of 20 cm at a frequency of 2 Hz. All the operations were performed under aseptic conditions to prevent the proliferation of bacteria during the storage.

After the storage for a given period of time, an aliquot of the platelet fraction was sampled and the number of platelets was measured. Prostaglandin E1 (Sigma Co.) was added to give a final concentration of 20 µg/ml and centrifuged at 750 g for 10 minutes. The supernatant was removed and the remainder was washed twice with HEPES-Tyrode's buffer containing prostaglandin E1 to remove the protected peptide. Finally, the platelets were suspended in preliminarily stored platelet-poor plasma. After the incubation for a given period of time, the aggregation ability of the platelets was determined by the method described above.

Figure 7:
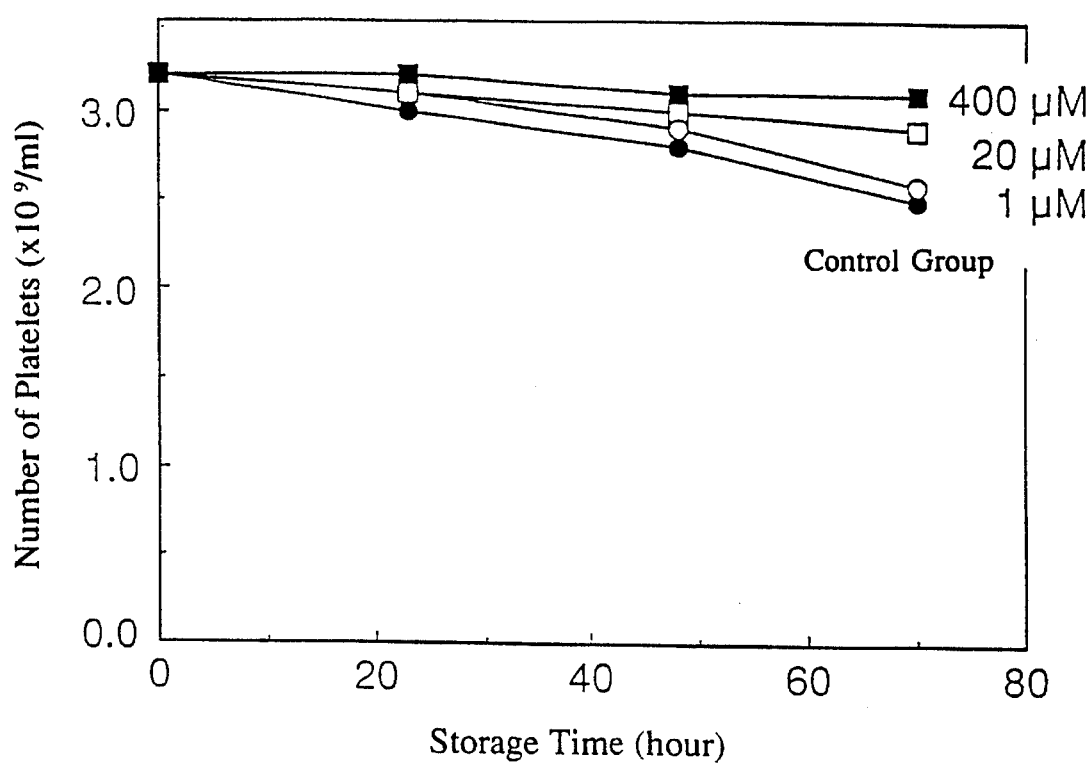
FIG. 7 is a graph showing the change in the number of platelets during storage.

FIG. 7 shows the change in the number of the platelets during the storage. In the control group to which only saline was added, the number of platelets decreased nearly in proportion to the storage time. In contrast, in the group to which the compound prepared in Example 9 (general formula (14)) was added, a significant inhibitory effect on the decrease in the number of platelets was observed compared to the control group. This protective effect was dependent on the concentration of the peptide added. When the peptide was added at a concentration of 400 µM, little decrease in the number of platelets was observed for the storage period of 72 hours.

Figure 8:
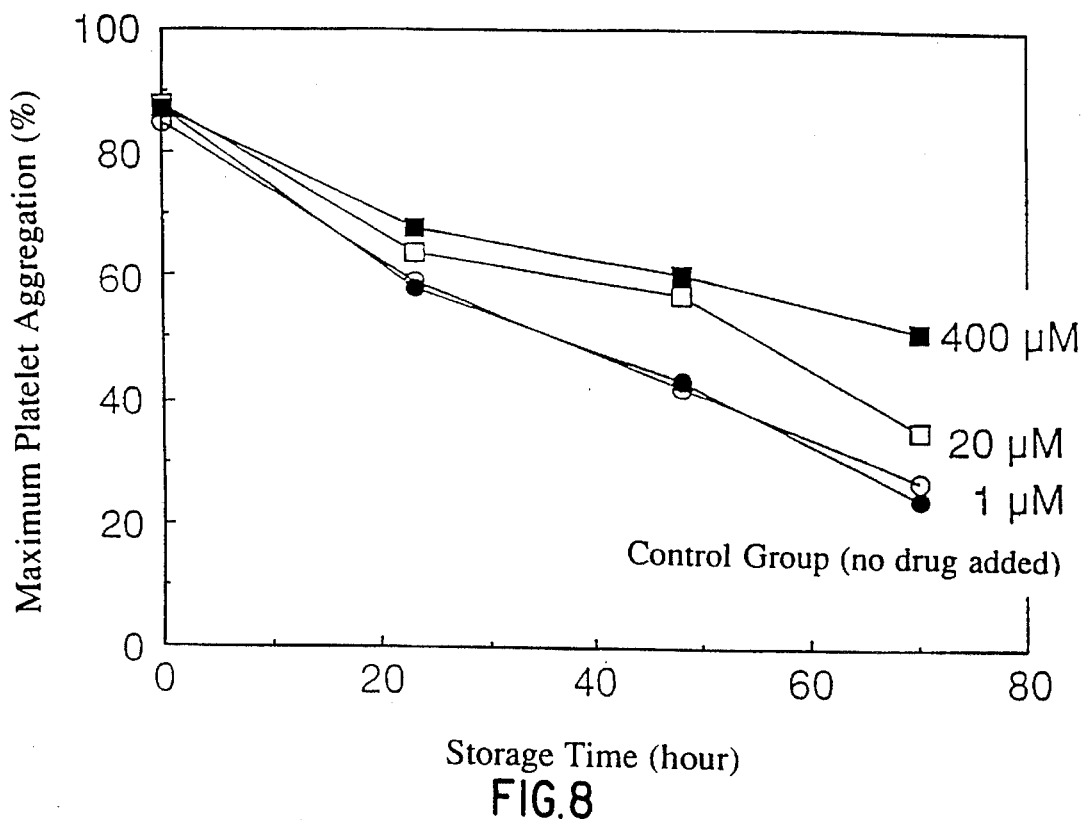
FIG. 8 is a graph showing the time-dependent change in aggregatory activity of human platelets during storage.
Figure 9A:
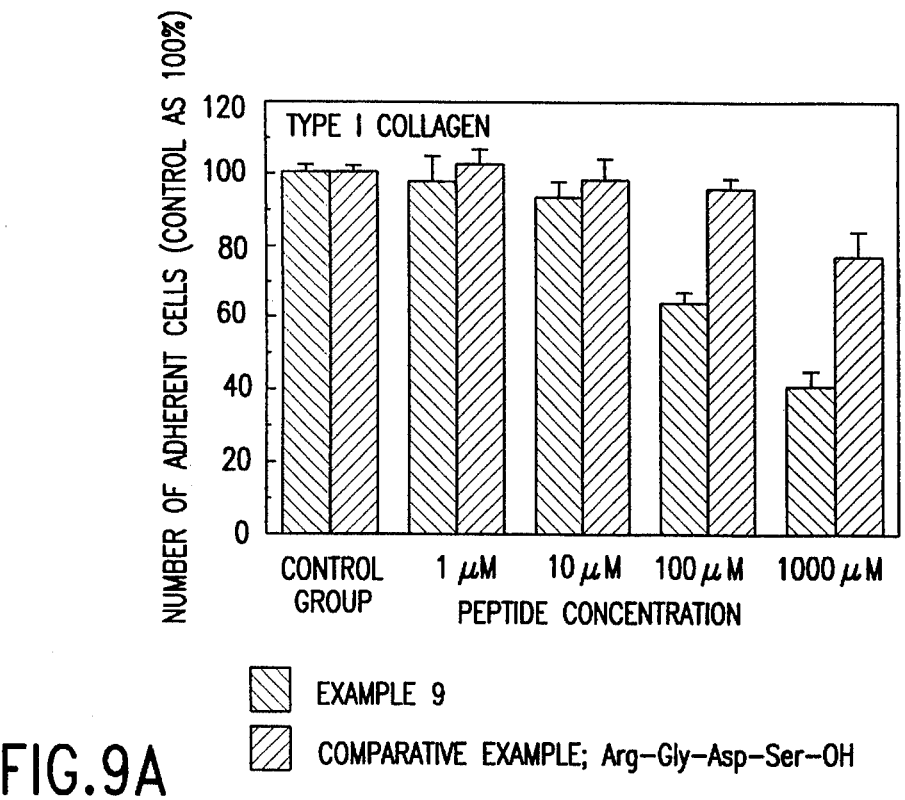
FIG. 9 is a set of graphs showing how the peptide prepared in Example 9 and a comparative peptide affected the adhesion of Hela cells to various extracellular matrix proteins.
Figure 9B:
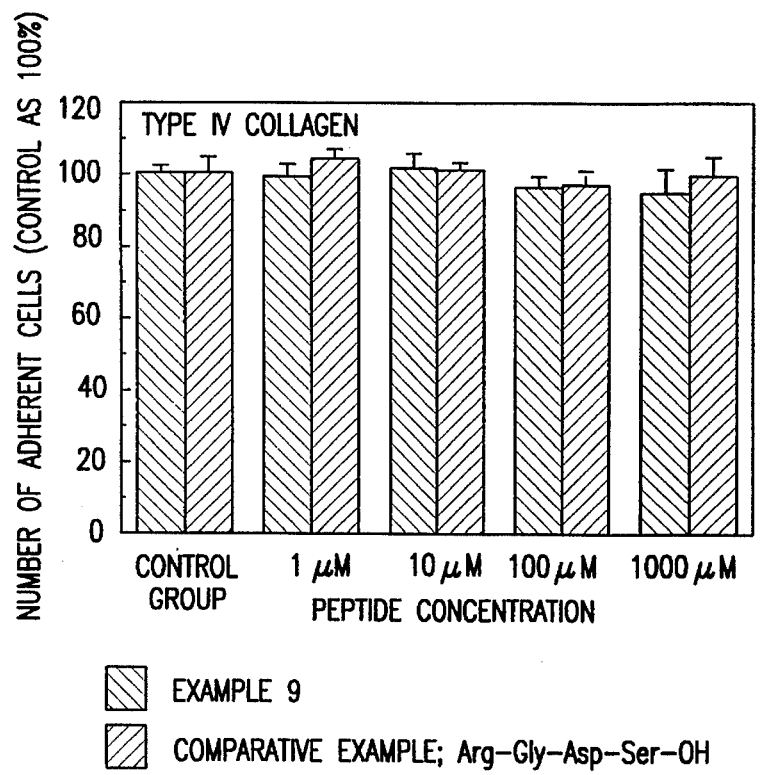
Figure 9C:
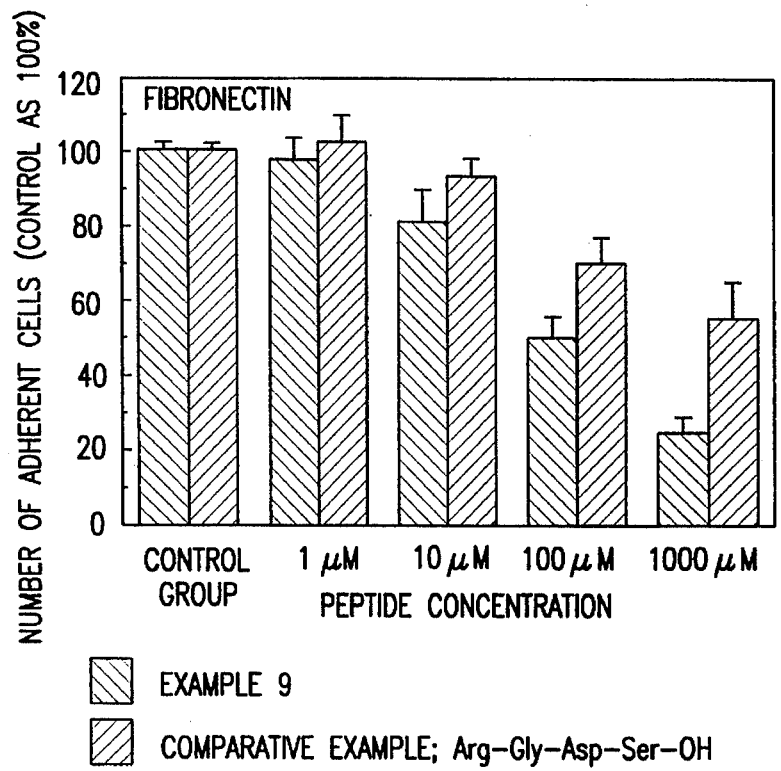
Figure 9D:
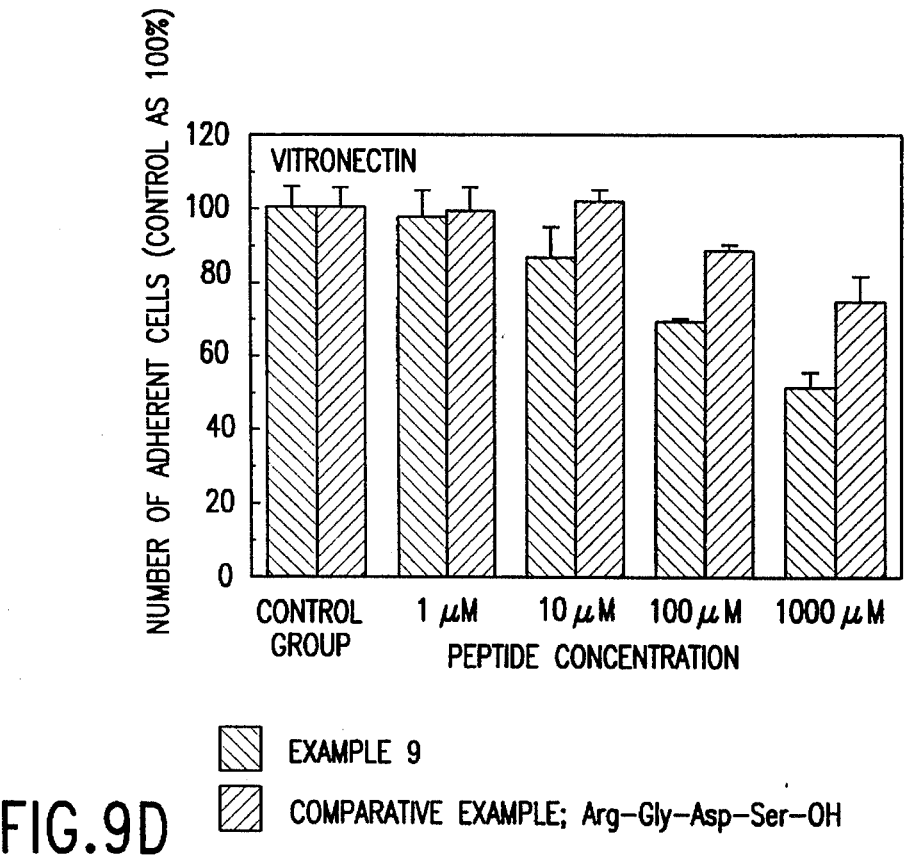
Figure 9E:
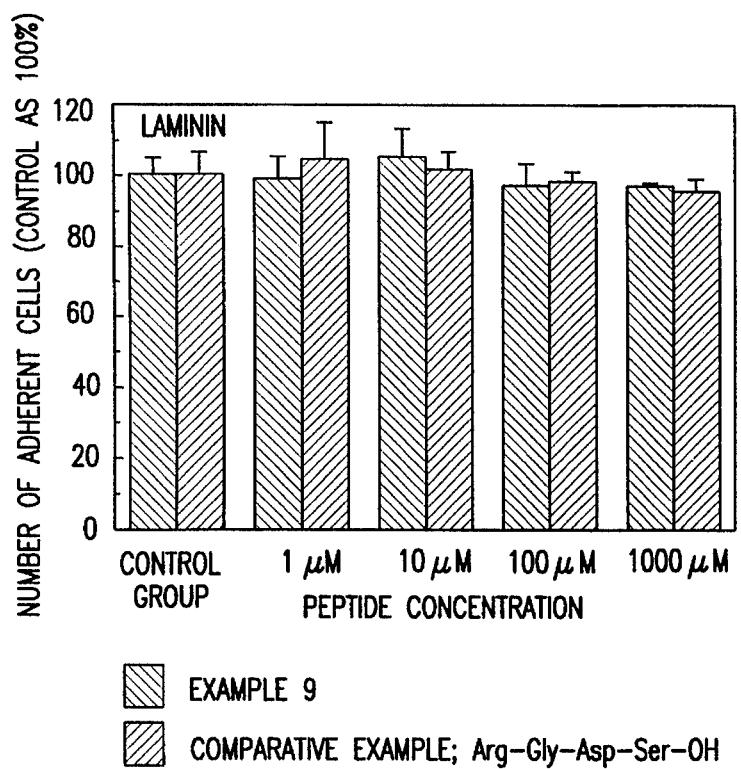
Figure 10A:
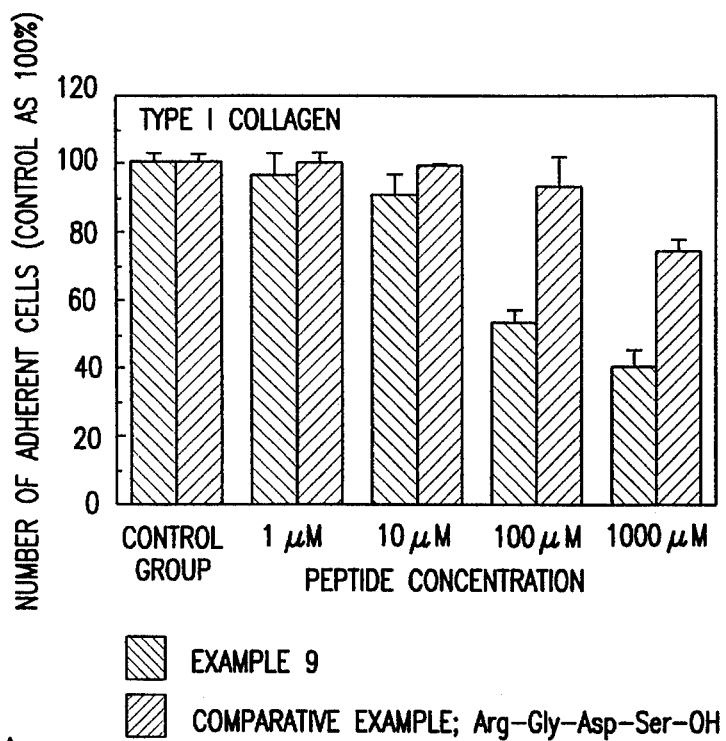
FIG. 10 is a set of graphs showing how the peptide prepared in Example 9 and a comparative peptide affected the adhesion of B16F10 melanoma cells to various extracellular matrix proteins.
Figure 10B:
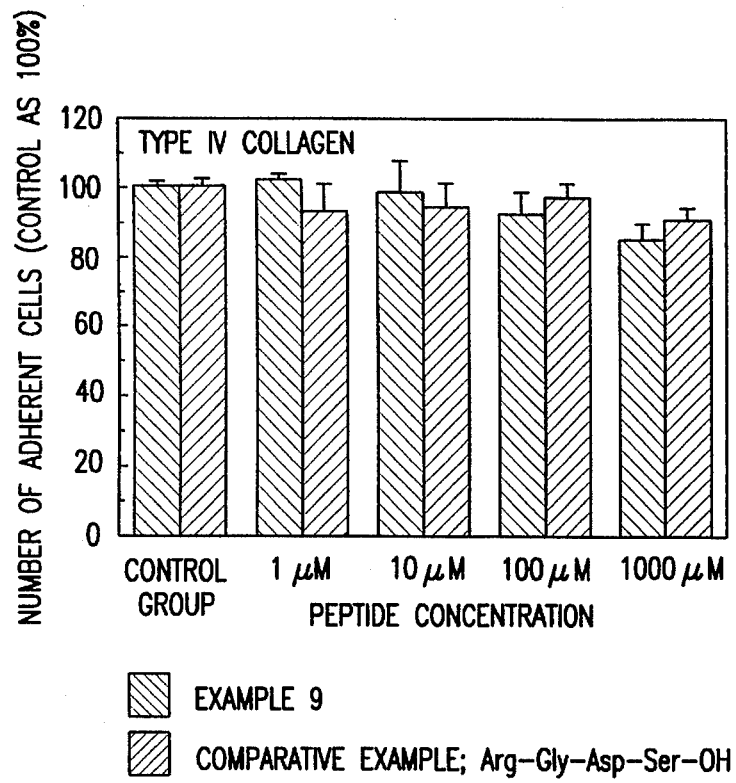
Figure 10C:
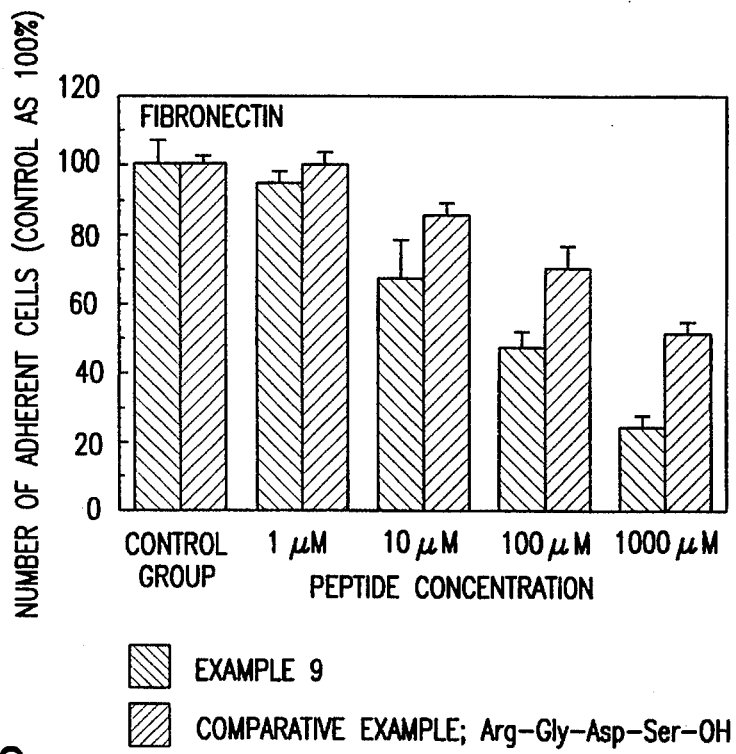
Figure 10D:
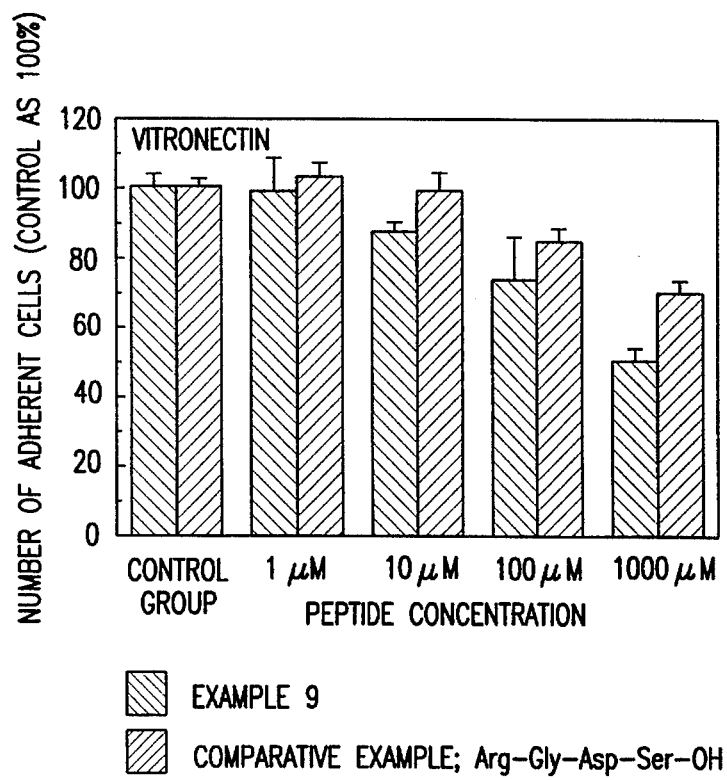
Figure 10E:
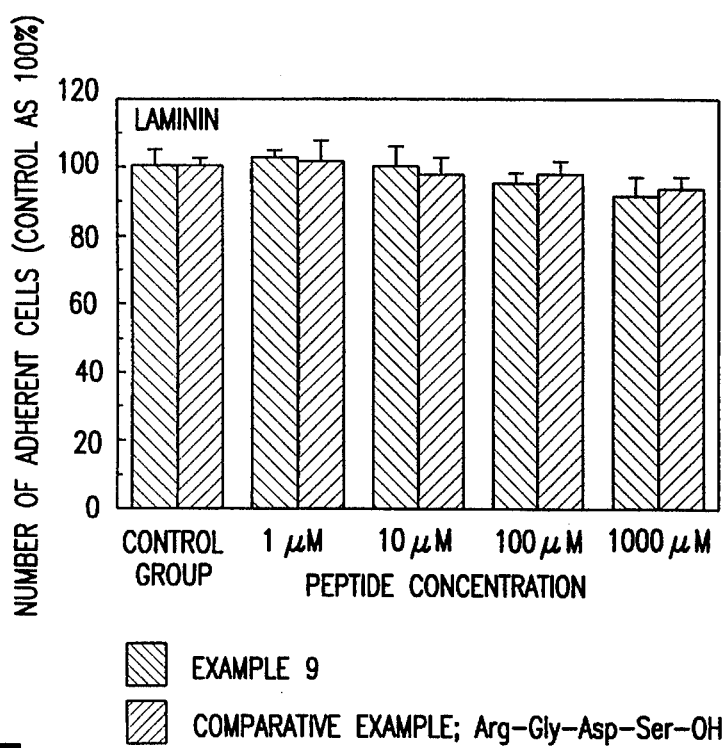

FIG. 8 shows the time-dependent change in the platelet aggregation ability during the storage. In the control group to which no drug was added, the aggregation activity of platelets decreased to 25% for the storage period of 72 hours. In the group to which the compound prepared in Example 9 (general formula (14)) was added, the decrease in the aggregation activity was significantly inhibited. The inhibitory effect on the decrease in the aggregation activity was dependent on the concentration of the peptide compound added. When the peptide was added at a concentration of 400 µM, 60–70% of the aggregation activity of platelets remained after the 72 hour storage.

As shown above, the addition of the peptide of the present invention to the platelet fraction created platelet protective effects during storage such as the inhibition of the decrease in the number of platelets, the platelet aggregation ability, and the like. It is already confirmed that even if peptide compounds heretofore in use such as RGDS, RGDF and the like are added to a platelet fraction, they are broken down in several hours due to the action of enzymes present in plasma, so it is clear that they cannot be used for long-term storage of platelets. On the other hand, compounds that are very stable and which will not be easily broken down in the body will inhibit all the functions of platelets in the body after transfusion and thereby lower the efficiency of blood transfusion. In contrast, the peptides of the present invention have desirable features such as high stability in a platelet fraction, high in vivo degradability and low toxicity and therefore, they are believed to be useful as highly excellent platelet protecting agents.

In addition, if the peptides of the present invention are administered in the form of acetate or phosphate, they are expected to manifest a buffering action and thereby produce inhibitory effects against the change of pH during the storage of a platelet fraction. Moreover, if the peptides of the present invention are not used alone but combined with other platelet aggregation-inhibiting agents having different modes of action such as aspirin, further effects can be expected.

[Experimental Example 5] Applicability of the Peptides of the Present Invention to Tumor Metastasis-Inhibiting Agents (1) Using type 1 collagen (Iwaki Glass, type I-c), type 4 collagen (Iwaki Glass, type IV), fibronectin (human-origin, Iwaki Glass), vitronectin (human-origin, Iwaki Glass) and laminin (mouse EHA sarcoma-origin, Iwaki Glass) as extracellular matrix proteins, experiments were performed to examine cell adhesion to a plastic plate on which those ectracellular matrix proteins had been adsorbed.

a) Preparation of an Extracellular Matrix Protein-Adsorbed Plate

Each of the collagens was diluted with saline (adjusted to pH 3.0 with hydrochloric acid) to prepare a dilution at a concentration of 100 µg/ml for use in adsorption. The remaining three proteins were diluted with PBS of pH 7.4 to prepare dilutions at a concentration of 20 µg/ml for further use.

In the preparation of a type 1 collagen adsorbed plate, the dilution of type 1 collagen (0.4 ml) was placed in each well of a 24-well plastic plate and maintained at 37° C. overnight to adsorb the type 1 collagen on the plate. For avoiding the non-specific binding of the cells, PBS containing 3% bovine serum albumin (Sigma Co.) was placed in each well and incubated at 37° C. for 1–2 hours. Finally, the plate was washed three times with PBS to prepare a type 1 collagen adsorbed plate. For the other extracellular matrix proteins, their adsorbed plates were prepared in the same manner.

b) Method for Determining Cell Adhesion-Inhibiting Activity

The peptide of the present invention was diluted with a serum-free EMEM medium (NIPPON SUISAN KAISHA, LTD.) to prepare a dilution series at concentrations of 5 mM, 0.5 mM, 50 µM and 5 µM. The serum-free EMEM medium (300 µl) had been placed preliminarily in the above prepared extracellular matrix protein adsorbed plates and 100 µl each of the peptide solutions at different concentrations were added to the respective wells. The experiment was performed in quadricate using 4 wells for each concentration of solution. In the control group to which no peptide was to be added, only the serum-free EMEM medium (100 µl) was added. Subsequently, a suspension of Hela cells or B16F10 melanoma cells ($5 \times 10^6$ cells/ml) was provided and added to the respective wells in 0.1-ml portions. The plastic plate was shaken horizontally in a gentle manner to stir and thereafter incubated in a $CO_2$ incubator for one hour.

c) Measurement of the Number of Adhesion Cells

After the incubation for one hour according to the method described above, all the liquid present in each well was removed and the wells were washed three times with PBS to remove non-adherent cells. Subsequently, a 3% paraformaldehyde solution (0.3 ml) was added to each well. After being left to stand at room temperature for 20 minutes, the plate was washed twice with PBS and then a 5% methylene blue solution was added thereto to stain the cells. After staining at room temperature for 20 minutes, the plate was fully washed with a 0.1M borate buffer (pH 8.5) to completely remove excess methylene blue. Finally, 1N hydrochloric acid (0.3 ml) was added and the plate was left to stand for 20 minutes. The concentration of methylene blue releasing from the cells was determined by a spectrophotometer on the basis of absorbance at 600 nm measured. In this measurement system, the number of cells adhering to the extracellular matrix proteins is proportional to the absorbance at 600 nm and therefore can be measured with precision.

(2) The inhibitory effect of comparative compound RGDS on cell adhesion was examined by the same method as in (1). FIGS. 9 and 10 show the effects of the compound prepared in Example 9 (general formula (14)) and the comparative compound RGDS on the adhesion of HeLa cells and B16F10 melanoma cells, respectively, to the various extracellular matrix proteins. As shown in these figures, there appeared scarcely any effect on the cell adhesion to laminin while the cell adhesion to the other extracelluler matrix proteins was inhibited depending on the concentration of the peptide represented by general formula (1) shown in Example 1. This effect was 10 to 100 times as strong as that of comparative compound RGDS. With respect to laminin, it has been said that not only RGD but also other sequences such as Tyr—Ile—Gly—Ser—Arg SEQ ID NO:13 and Ile—Lys—Val—Ala—Val SEQ ID NO:14 relate to the cell adhesion and a receptor (integrin) specific to each of these sequences has been found. In the experiments whose results are shown in FIGS. 9 and 10, the cell adhesion to laminin was hardly inhibited and this is probably because a large number of these laminin-specific receptors were expressed on the surfaces of HeLa cells or B16F10 cells.

As shown above, the peptides of the present invention inhibit the adhesion of various tumor cells to extracellular matrix proteins. This indicates that the peptides of the present invention can inhibit the adhesion of tumor cells to a blood vessel basement membrane, strongly suggesting the potency of the peptides as tumor metastasis-inhibiting agents. The compounds of the present invention have very low toxicity and therefore, are tolerant of long-term administration unlike currently used, highly toxic anti-tumor drugs. Therefore, one may expect with good reason that the peptides of the present invention are used as quite a new type of tumor metastasis-inhibiting agents.

[Experimental Example 6] Acute Toxicity Test

The peptides of the present invention were intravenously injected into a mouse in an amount of 100 mg/Kg but no toxicity was observed.

[Formulation Example 1]

Each of the peptides prepared in Examples (100 mg) was dissolved in 100 ml of saline. Under aseptic conditions, the obtained solution was charged in a 2.5 ml volume ampule and the ampule was sealed to prepare an injection preparation.

[Formulation Example 2]

A mixture (1 ml) of ethanol and water was added to a mixture consisting of one of the peptides prepared in Examples (500 mg), crystalline cellulose (50 mg) and lactose (450 mg) and blended intimately. The obtained mixture was granulated by a conventional method to prepare granules.

INDUSTRIAL APPLICABILITY

According to the present invention, novel peptides having inhibitory effects on platelet aggregation and blood coagulation, and platelet aggregation-inhibiting agents that are effective in thrombosis during and after the treatment of thrombolysis and in thromboembolism and that can further prevent reobstruction and myocardical infarction, as well as blood coagulation-inhibiting agents that can inhibit blood coagulation which is the main cause of thrombus formation during an extracorporeal circulation, which agents comprise the peptides as active ingredients, are provided.

In addition, according to the present invention, agents for protecting platelet preparations for blood transfusion, cell adhesion-inhibiting agents and tumor metastasis-inhibiting agents are provided.

Moreover, according to the present invention, platelet preparation packs for blood transfusion, characterized in that agents for protecting platelet preparations for blood transfusion are contained in platelet preparations for blood transfusion in packs, are provided.

We claim:

1. A peptide, a peptide derivative or a salt thereof, that is represented by the following general formula:

$$A—B—Arg—Gly—Asp—C—D \qquad (I)$$

wherein A is proline, thioproline, hydroxyproline, dehydroproline, 2-oxo-4-thiazolidine carboxylic acid, N-alkyl glycine or an imino acid derivative represented by the following general formula:

$$\begin{array}{c}(CH_2)_m\\ \diagdown\\ N—(CH_2)_n—CO—\\ |\\ R_1\end{array} \qquad (II)$$

wherein $R_1$ is a hydrogen atom, $—(CH_2)_p CH_3$ or $—CO—(CH_2)_p CH_3$ group (p is an integer of 0–5), m is an integer of 2–5, n is an integer of 0–2, tryptophan or a tryptophan derivative represented by the following general formula:

$$(III)$$

wherein $R_2$ is a hydrogen atom or an alkyl group, $R_3$ is a hydrogen atom or an O-alkyl group, $R_4$ is a hydrogen atom or an alkyl group, $R_5$ is a hydrogen atom, an amino or amino acyl group, and q is an integer of 0–3, pyroglutamic acid or 2-azetidinone- 4-carboxylic acid, B is serine, glycine, valine, alanine, threonine or β-alanine, C is an amino acid group having a hydrophobic functional group, and D is a hydroxy or amino group.

2. A peptide, peptide derivative or salt thereof, that is represented by the following general formula:

$$A—B—Arg—Gly—Asp—C—D \qquad (I)$$

wherein A is orotic acid or hydroorotic acid, B is an amino acid, C is an amino acid having a hydrophobic functional group, and D is a hydroxy or amino group.

3. The peptide, peptide derivative or salt thereof according to claim 1, wherein said C is tryptophan or phenylalanine.

4. A platelet aggregation-inhibiting agent comprising the peptide, peptide derivative or salt thereof according to claim 1 as an active ingredient.

5. A blood coagulation-inhibiting agent for extracorporeal circulation comprising the peptide, peptide derivative or salt thereof according to claim 1 as an active ingredient.

6. A cell adhesion-inhibiting agent comprising the peptide, peptide derivative or salt thereof according to claim 1 as an active ingredient.

7. A tumor metastasis-inhibiting agent comprising the peptide, peptide derivative or salt thereof according to claim 1 as an active ingredient.

8. An agent for protecting platelet preparations for blood transfusion comprising the peptide, peptide derivative or salt thereof according to claim 1 as an active ingredient.

9. The peptide, peptide derivative or salt thereof according to claim 2, wherein said B is serine, glycine, valine, alanine, threonine or β-alanine.

10. The peptide, peptide derivative or salt thereof according to claim 2, wherein said C is tryptophan or phenylalanine.

11. The peptide, peptide derivative or salt thereof according to claim 9, wherein said C is tryptophan or phenylalanine.

12. A platelet aggregation-inhibiting agent comprising the peptide, peptide derivative or salt thereof according to claim 2 as an active ingredient.

13. A platelet aggregation-inhibiting agent comprising the peptide, peptide derivative or salt thereof according to claim 3 as an active ingredient.

14. A platelet aggregation-inhibiting agent comprising the peptide, peptide derivative or salt thereof according to claim 10 as an active ingredient.

15. A platelet aggregation-inhibiting agent comprising the peptide, peptide derivative or salt thereof according to claim 9 as an active ingredient.

16. A platelet aggregation-inhibiting agent comprising the peptide, peptide derivative or salt thereof according to claim 11 as an active-ingredient.

17. A blood coagulation-inhibiting agent for extracorporeal circulation comprising the peptide, peptide derivative or salt thereof according to claim 2 as an active ingredient.

18. A blood coagulation-inhibiting agent for extracorporeal circulation comprising the peptide, peptide derivative or salt thereof according to claim 3 as an active ingredient.

19. A blood coagulation-inhibiting agent for extracorporeal circulation comprising the peptide, peptide derivative or salt thereof according to claim 10 as an active ingredient.

20. A blood coagulation-inhibiting agent for extracorporeal circulation comprising the peptide, peptide derivative or salt thereof according to claim 9 as an active ingredient.

21. A blood coagulation-inhibiting agent for extracorporeal circulation comprising the peptide, peptide derivative or salt thereof according to claim 11 as an active ingredient.

22. A cell adhesion-inhibiting agent comprising the peptide, peptide derivative or salt thereof according to claim 2 as an active ingredient.

23. A cell adhesion-inhibiting agent comprising the peptide, peptide derivative or salt thereof according to claim 3 as an active ingredient.

24. A cell adhesion-inhibiting agent comprising the peptide, peptide derivative or salt thereof according to claim 10 as an active ingredient.

25. A cell adhesion-inhibiting agent comprising the peptide, peptide derivative or salt thereof according to claim 9 as an active ingredient.

26. A cell adhesion-inhibiting agent comprising the peptide, peptide derivative or salt thereof according to claim 11 as an active ingredient.

27. A tumor metastasis-inhibiting agent comprising the peptide, peptide derivative or salt thereof according to claim 2 as an active ingredient.

28. A tumor metastasis-inhibiting agent comprising the peptide, peptide derivative or salt thereof according to claim 3 as an active ingredient.

29. A tumor metastasis-inhibiting agent comprising the peptide, peptide derivative or salt thereof according to claim 10 as an active ingredient.

30. A tumor metastasis-inhibiting agent comprising the peptide, peptide derivative or salt thereof according to claim 9 as an active ingredient.

31. A tumor metastasis-inhibiting agent comprising the peptide, peptide derivative or salt thereof according to claim 11 as an active ingredient.

32. An agent for protecting platelet preparations for blood transfusion comprising the peptide, peptide derivative or salt thereof according to claim 2 as an active ingredient.

33. An agent for protecting platelet preparations for blood transfusion comprising the peptide, peptide derivative or salt thereof according to claim 3 as an active ingredient.

34. An agent for protecting platelet preparations for blood transfusion comprising the peptide, peptide derivative or salt thereof according to claim 10 as an active ingredient.

35. An agent for protecting platelet preparations for blood transfusion comprising the peptide, peptide derivative or salt thereof according to claim 9 as an active ingredient.

36. An agent for protecting platelet preparations for blood transfusion comprising the peptide, peptide derivative or salt thereof according to claim 11 as an active ingredient.

* * * * *